United States Patent
Meltzer et al.

(10) Patent No.: US 9,028,776 B2
(45) Date of Patent: May 12, 2015

(54) DEVICE FOR STRETCHING A POLYMER IN A FLUID SAMPLE

(71) Applicant: PathoGenetix, Inc., Woburn, MA (US)

(72) Inventors: Robert H. Meltzer, Chelmsford, MA (US); Joshua W. Griffis, Gardner, MA (US)

(73) Assignee: Toxic Report LLC, Watertown, MA (US)

( * ) Notice: Subject to any disclaimer, the term of this patent is extended or adjusted under 35 U.S.C. 154(b) by 0 days.

(21) Appl. No.: 13/862,129

(22) Filed: Apr. 12, 2013

(65) Prior Publication Data

US 2013/0309780 A1 Nov. 21, 2013
US 2014/0234985 A9 Aug. 21, 2014

Related U.S. Application Data

(60) Provisional application No. 61/625,745, filed on Apr. 18, 2012, provisional application No. 61/784,399, filed on Mar. 14, 2013.

(51) Int. Cl.
*B01L 3/00* (2006.01)
*G01N 1/28* (2006.01)

(52) U.S. Cl.
CPC .......... *G01N 1/286* (2013.01); *B01L 3/502761* (2013.01); *B01L 2200/0663* (2013.01); *B01L 2300/0816* (2013.01); *B01L 2300/0867* (2013.01)

(58) Field of Classification Search
USPC ................................................. 422/502–507
See application file for complete search history.

(56) References Cited

U.S. PATENT DOCUMENTS

| | | |
|---|---|---|
| 4,147,621 A | 4/1979 | Giddings |
| 4,833,332 A | 5/1989 | Robertson, Jr. et al. |
| 4,979,824 A | 12/1990 | Mathies et al. |
| 5,079,169 A | 1/1992 | Chu et al. |
| 5,141,651 A | 8/1992 | Giddings |
| 5,169,511 A | 12/1992 | Allington et al. |
| 5,274,240 A | 12/1993 | Mathies et al. |
| 5,304,487 A | 4/1994 | Wilding et al. |
| 5,324,401 A | 6/1994 | Yeung et al. |
| 5,356,776 A | 10/1994 | Kambara et al. |
| 5,374,527 A | 12/1994 | Grossman |
| 5,427,663 A | 6/1995 | Austin et al. |
| 5,449,917 A | 9/1995 | Clements |
| 5,538,898 A | 7/1996 | Wickramasinghe et al. |

(Continued)

FOREIGN PATENT DOCUMENTS

| | | |
|---|---|---|
| EP | 0391674 A2 | 10/1990 |
| EP | 1 380 337 A2 | 1/2004 |

(Continued)

OTHER PUBLICATIONS

Akerman et al., Electrophoretic orientation of DNA detected by linear dichroism spectroscopy. J. Chem Soc. D. Chem. Commun. 1985:422.

(Continued)

*Primary Examiner* — Jan Ludlow
(74) *Attorney, Agent, or Firm* — Wolf, Greenfield & Sacks, P.C.

(57) ABSTRACT

The invention provides structures and methods that allow polymers of any length, including nucleic acids, to be stretched into a long, linear conformation for further analysis.

23 Claims, 8 Drawing Sheets

(56) References Cited

U.S. PATENT DOCUMENTS

| | | |
|---|---|---|
| 5,599,664 A | 2/1997 | Schwartz |
| 5,601,694 A | 2/1997 | Maley et al. |
| 5,612,181 A | 3/1997 | Fourmentin-Guilbert et al. |
| 5,675,155 A | 10/1997 | Pentoney, Jr. et al. |
| 5,699,157 A | 12/1997 | Parce |
| 5,707,797 A | 1/1998 | Windle |
| 5,711,861 A | 1/1998 | Ward et al. |
| 5,711,868 A | 1/1998 | Maley et al. |
| 5,720,928 A | 2/1998 | Schwartz |
| 5,795,782 A | 8/1998 | Church et al. |
| 5,798,215 A | 8/1998 | Cathey et al. |
| 5,837,115 A | 11/1998 | Austin et al. |
| 5,840,862 A | 11/1998 | Bensimon et al. |
| 5,843,767 A | 12/1998 | Beattie |
| 5,846,724 A | 12/1998 | Bensimon et al. |
| 5,846,727 A | 12/1998 | Soper et al. |
| 5,846,832 A | 12/1998 | Oefner et al. |
| 5,851,769 A | 12/1998 | Gray et al. |
| 5,867,266 A | 2/1999 | Craighead |
| 5,879,625 A | 3/1999 | Roslaniec et al. |
| 5,880,473 A | 3/1999 | Ginestet |
| 5,906,723 A | 5/1999 | Mathies et al. |
| 5,971,158 A | 10/1999 | Yager et al. |
| 6,001,229 A | 12/1999 | Ramsey |
| 6,008,892 A | 12/1999 | Kain et al. |
| 6,015,714 A | 1/2000 | Baldarelli et al. |
| 6,054,327 A | 4/2000 | Bensimon et al. |
| 6,071,394 A | 6/2000 | Cheng et al. |
| 6,090,251 A | 7/2000 | Sundberg et al. |
| 6,100,541 A | 8/2000 | Nagle et al. |
| 6,120,666 A | 9/2000 | Jacobson et al. |
| 6,139,800 A | 10/2000 | Chandler |
| 6,150,089 A | 11/2000 | Schwartz |
| 6,193,647 B1 | 2/2001 | Beebe et al. |
| 6,210,896 B1 | 4/2001 | Chan |
| 6,210,973 B1 | 4/2001 | Pettit |
| 6,214,246 B1 | 4/2001 | Craighead |
| 6,263,286 B1 | 7/2001 | Gilmanshin et al. |
| 6,294,136 B1 | 9/2001 | Schwartz |
| 6,319,469 B1 | 11/2001 | Mian et al. |
| 6,344,319 B1 | 2/2002 | Bensimon et al. |
| 6,355,420 B1 | 3/2002 | Chan |
| 6,403,311 B1 | 6/2002 | Chan |
| 6,432,630 B1 | 8/2002 | Blankenstein |
| 6,444,992 B1 | 9/2002 | Kauvar et al. |
| 6,506,609 B1 | 1/2003 | Wada et al. |
| 6,562,307 B1 | 5/2003 | Schuch et al. |
| 6,605,454 B2 | 8/2003 | Barenburg et al. |
| 6,641,708 B1 | 11/2003 | Becker et al. |
| 6,660,480 B2 | 12/2003 | Ramsey et al. |
| 6,696,022 B1 | 2/2004 | Chan et al. |
| 6,762,059 B2 | 7/2004 | Chan et al. |
| 6,766,817 B2 | 7/2004 | da Silva |
| 6,767,731 B2 | 7/2004 | Hannah |
| 6,770,182 B1 | 8/2004 | Griffiths et al. |
| 6,772,070 B2 | 8/2004 | Gilmanshin et al. |
| 6,790,671 B1 | 9/2004 | Austin et al. |
| 6,927,065 B2 | 8/2005 | Chan et al. |
| 7,262,859 B2 | 8/2007 | Larson et al. |
| 7,282,330 B2 | 10/2007 | Zhao et al. |
| 7,351,538 B2 | 4/2008 | Fuchs et al. |
| 7,371,520 B2 | 5/2008 | Zhao et al. |
| 7,402,422 B2 | 7/2008 | Fuchs et al. |
| 7,595,160 B2 | 9/2009 | White et al. |
| 7,828,948 B1 | 11/2010 | Hatch et al. |
| 7,888,011 B2 | 2/2011 | Nilsen et al. |
| 7,977,048 B2 | 7/2011 | Gilmanshin |
| 8,114,636 B2 | 2/2012 | Agnew et al. |
| 8,168,380 B2 | 5/2012 | Chan |
| 8,361,716 B2 | 1/2013 | Patil |
| 8,423,294 B2 | 4/2013 | Nadel et al. |
| 8,518,705 B2 | 8/2013 | Chan et al. |
| 2001/0030130 A1 | 10/2001 | Ricco et al. |
| 2001/0055817 A1 | 12/2001 | Malmqvist et al. |
| 2002/0008028 A1 | 1/2002 | Jacobson et al. |
| 2002/0029814 A1 | 3/2002 | Unger et al. |
| 2002/0034748 A1 | 3/2002 | Quake et al. |
| 2002/0039737 A1 | 4/2002 | Chan et al. |
| 2002/0055167 A1 | 5/2002 | Pourahmadi et al. |
| 2002/0058332 A1 | 5/2002 | Quake et al. |
| 2002/0072243 A1 | 6/2002 | Craighead et al. |
| 2002/0079008 A1 | 6/2002 | Chien et al. |
| 2002/0109844 A1 | 8/2002 | Christel et al. |
| 2002/0110495 A1 | 8/2002 | Hunt et al. |
| 2002/0110818 A1 | 8/2002 | Chan |
| 2002/0119455 A1 | 8/2002 | Chan |
| 2002/0187508 A1 | 12/2002 | Wong |
| 2002/0197639 A1 | 12/2002 | Shia et al. |
| 2003/0058440 A1 | 3/2003 | Scott et al. |
| 2003/0059822 A1 | 3/2003 | Chan et al. |
| 2003/0104466 A1 | 6/2003 | Knapp et al. |
| 2003/0124623 A1 | 7/2003 | Yager et al. |
| 2003/0162181 A1 | 8/2003 | Yang et al. |
| 2003/0215864 A1 | 11/2003 | Gilmanshin et al. |
| 2003/0235854 A1 | 12/2003 | Chan et al. |
| 2004/0009612 A1 | 1/2004 | Zhao et al. |
| 2004/0028580 A1 | 2/2004 | Futami et al. |
| 2004/0053399 A1 | 3/2004 | Gilmanshin |
| 2004/0126279 A1 | 7/2004 | Renzi et al. |
| 2004/0166025 A1 | 8/2004 | Chan et al. |
| 2004/0188254 A1 | 9/2004 | Spaid |
| 2004/0214211 A1 | 10/2004 | Gilmanshin et al. |
| 2004/0235014 A1 | 11/2004 | Nadel et al. |
| 2005/0009066 A1 | 1/2005 | Connolly |
| 2005/0042665 A1 | 2/2005 | Gilmanshin et al. |
| 2005/0112595 A1 | 5/2005 | Zhao et al. |
| 2005/0112606 A1 | 5/2005 | Fuchs et al. |
| 2005/0112620 A1 | 5/2005 | Chan |
| 2005/0112671 A1 | 5/2005 | Maletta et al. |
| 2005/0123944 A1 | 6/2005 | Neely et al. |
| 2005/0123974 A1 | 6/2005 | Gilmanshin et al. |
| 2005/0142565 A1 | 6/2005 | Samper et al. |
| 2005/0142595 A1 | 6/2005 | Maletta et al. |
| 2005/0148064 A1 | 7/2005 | Yamakawa et al. |
| 2005/0153354 A1 | 7/2005 | Gilmanshin |
| 2005/0196790 A1 | 9/2005 | Rooke |
| 2005/0221408 A1 | 10/2005 | Nalefski et al. |
| 2006/0078915 A1 | 4/2006 | Fuchs et al. |
| 2006/0134679 A1 | 6/2006 | Larson |
| 2006/0160209 A1 | 7/2006 | Larson et al. |
| 2006/0160231 A1 | 7/2006 | Nadel et al. |
| 2006/0191792 A1 | 8/2006 | Herr et al. |
| 2006/0204978 A1 | 9/2006 | Nilsen et al. |
| 2006/0211055 A1 | 9/2006 | Hafeman et al. |
| 2006/0228747 A1 | 10/2006 | Fuchs et al. |
| 2006/0292616 A1 | 12/2006 | Neely et al. |
| 2006/0292617 A1 | 12/2006 | Neely et al. |
| 2007/0031961 A1 | 2/2007 | Ho et al. |
| 2007/0042406 A1 | 2/2007 | Yantz et al. |
| 2007/0128083 A1 | 6/2007 | Yantz et al. |
| 2007/0166743 A1 | 7/2007 | Gilmanshin |
| 2008/0003689 A1 | 1/2008 | Lee et al. |
| 2008/0085521 A1 | 4/2008 | Knapp et al. |
| 2008/0085552 A1 | 4/2008 | Larson et al. |
| 2008/0103296 A1 | 5/2008 | Zhao et al. |
| 2008/0254549 A1 | 10/2008 | Fuchs et al. |
| 2008/0280285 A1 | 11/2008 | Chen et al. |
| 2009/0035770 A1 | 2/2009 | Mathies et al. |
| 2010/0035247 A1 | 2/2010 | Burton |
| 2010/0112576 A1 | 5/2010 | Patil |
| 2010/0116025 A1 | 5/2010 | Gouveia et al. |
| 2010/0120101 A1 | 5/2010 | Patil et al. |
| 2010/0234237 A1 | 9/2010 | Yoo |
| 2010/0294665 A1 | 11/2010 | Allen et al. |
| 2012/0283955 A1 | 11/2012 | Cameron et al. |
| 2013/0000738 A1 | 1/2013 | Krogmeier et al. |
| 2013/0266935 A1 | 10/2013 | Patil |
| 2013/0288234 A1 | 10/2013 | Harris et al. |

(56) References Cited

U.S. PATENT DOCUMENTS

| | | | |
|---|---|---|---|
| 2013/0295686 A1 | 11/2013 | Meltzer et al. | |
| 2014/0011686 A1 | 1/2014 | Gilmanshin | |
| 2014/0135489 A1 | 5/2014 | Harris et al. | |

FOREIGN PATENT DOCUMENTS

| | | |
|---|---|---|
| JP | 63196845 | 8/1988 |
| WO | WO 93/22463 A2 | 11/1993 |
| WO | WO 94/16313 A2 | 7/1994 |
| WO | WO 97/06278 A1 | 2/1997 |
| WO | WO 98/10097 A2 | 3/1998 |
| WO | WO 98/35012 A2 | 8/1998 |
| WO | WO 99/09042 A2 | 2/1999 |
| WO | WO 00/09757 A1 | 2/2000 |
| WO | WO 00/50172 A1 | 8/2000 |
| WO | WO 00/56444 A2 | 9/2000 |
| WO | WO 00/70080 A1 | 11/2000 |
| WO | WO 01/28700 A1 | 4/2001 |
| WO | WO 02/29106 A2 | 4/2002 |
| WO | WO 02/099398 A1 | 12/2002 |
| WO | WO 02/101095 A1 | 12/2002 |
| WO | WO 02/101353 A2 | 12/2002 |
| WO | WO 03/000416 A2 | 1/2003 |
| WO | WO 03/025540 A2 | 3/2003 |
| WO | WO 03/091455 A1 | 11/2003 |
| WO | WO 03/100101 A1 | 12/2003 |
| WO | WO 2004/007692 A2 | 1/2004 |
| WO | WO 2004/048514 A2 | 6/2004 |
| WO | WO 2004/066185 A1 | 8/2004 |
| WO | WO 2005/078137 A1 | 8/2005 |
| WO | WO 2005/085849 A2 | 9/2005 |
| WO | WO 2007/056250 A2 | 5/2007 |
| WO | WO 2008/024483 A2 | 2/2008 |
| WO | WO 2009/009127 A2 | 1/2009 |

OTHER PUBLICATIONS

Bakajin, et al., Electrohydrodynamic Stretching of DNA in Confined Environments. Phys. Rev. Lett. Mar. 23, 1998;80(12):2737-2740.

Bello et al, Electroosmosis of polymer solutions in fused silica capillaries. Electrophoresis. May 1994;15(5):623-6.

Bensimon, et al., "Alignment and Sensitive Detection of DNA by a Moving Interface," (1994), Science vol. 265, pp. 2096-2098.

Bensimon, et al., "Stretching DNA with a Receding Meniscus: Experiments and Models," (1995), Phys. Rev. Lett. vol. 74, pp. 4754-4757.

Bezrukov et al., Counting polymers moving through a single ion channel. Nature. Jul. 28, 1994;370(6487):279-81.

Burton et al., A microfluidic chip-compatible bioassay based on single-molecule detection with high sensitivity and multiplexing. Lab Chip. Apr. 7, 2010;10(7):843-51. Epub Jan. 14, 2010.

Bustamante et al., Direct observation and manipulation of single DNA molecules using fluorescence microscopy. Annu Rev Biophys Biophys Chem. 1991;20:415-46.

Chan et al., DNA mapping technology based on microfluidic stretching and single-molecule detection of motif tags. Biophys J. 2003;84:302A. Poster 1470. Board #B725.

Chan et al., DNA mapping using microfluidic stretching and single-molecule detection of fluorescent site-specific tags. Genome Res. Jun. 2004;14(6):1137-46.

Cluzel et al., DNA: an extensible molecule. Science. Feb. 9, 1996;271(5250):792-4.

Griffis et al., High-throughput genome scanning in constant tension fluidic funnels. Lab Chip. Jan. 21, 2013;13(2):240-51. doi: 10.1039/c2lc40943g. Epub Dec. 3, 2012. Supplemental Material Included. 8 pgs.

Gurrieri et al., Purification and staining of intact yeast DNA chromosomes and real-time observation of their migration during gel electrophoresis. Biochem J. Aug. 15, 1997;326 ( Pt 1):131-8.

Hatfield, et al., "Dynamic Properties of an Extended Polymer in Solution," (1999), Phys. Rev. Lett. vol. 82, pp. 3548-3551.

Herrick et al., Single molecule analysis of DNA replication. Biochimie. Aug.-Sep. 1999;81(8-9):859-71.

Holzwarth, the acceleration of linear DNA during pulsed-field gel electrophoresis. Biopolymers. Jun. 1989;28(6):1043-58.

Jo et al., A single-molecule barcoding system using nanoslits for DNA analysis. Proc Natl Acad Sci U S A. Feb. 20, 2007;104(8):2673-8. Epub Feb. 12, 2007.

Krogmeier et al., A Microfluidic Device for Concentrating High Molecular Weight DNA. Mar. 2, 2009; 315a. 1608 Pos. Board B452. Abstract.

Kwok et al., An Integrated Multifunction Lab-on-a-Chip Platform for High Throughput Optical Mapping for DNA. Biophysical Society 53rd Annual Meeting. Feb. 28-Mar. 4, 2009. Boston. Poster.

Kwok et al., An Integrated Multifunction Lab-on-a-Chip Platform for High Throughput Optical Mapping for DNA. Nanotechnology. 2009;48a. 244—Pos. Board B123. Abstract.

Larson et al., Single DNA molecule stretching in sudden mixed shear and elongational microflows. Lab Chip. 2006;6(9):1187-1199.

Marko, DNA under high tension: overstretching, undertwisting, and relaxation dynamics. Physical Rev E. Feb. 1998;57(2):2134-2149.

Michalet et al., Dynamic molecular combing: stretching the whole human genome for high-resolution studies. Science, 1997;277(5331):1518-1523.

Oana et al., Visualization of a specific sequence on a single large DNA molecule using fluorescence microscopy based on a new DNA-stretching method. Biochem Biophys Res Commun. Nov. 1999;265(1):140-3.

Papkov et al., A single-molecule system for detection and quantification of proteins with robust capture units and potential for high multiplexing. Biophysical Society 53rd Annual Meeting. Feb. 28-Mar. 4, 2009. Boston. Poster.

Perkins et al., Single Polymer Dynamics in an Elongational Flow. Science 1997;276:2016-2021.

Perkins et al., Stretching of a Single Tethered Polymer in a Uniform Flow. Science. 1995;268:83-87.

Phillips et al., Application of single molecule technology to rapidly map long DNA and study the conformation of stretched DNA. Nuc Acids Res. 2005;33(18):5829-37.

Rouzina et al., Force-induced melting of the DNA double helix. Biophys J. Feb. 2001;80:894-900.

Schafer et al., Single molecule DNA restriction in the light microscope. Single Mol. 2000;1(1):33-40.

Smith et al., "Single-polymer dynamics in steady shear flow." Science. 1999;283:1724-1727.

Smith et al., "Direct Mechanical Measurements of the Elasticity of Single DNA Molecules by Using Magnetic Beads," (1992), Science vol. 258, pp. 1122-1126.

Smith et al., "Response of Flexible Polymers to a Sudden Elongational Flow," (1998), Science vol. 281, pp. 1335-1340.

Sturm et al., Direct observation of DNA chain orientation and relaxation by electric birefringence: implications for the mechanism of separation during pulsed-field gel electrophoresis. Phys Rev Lett. 1989;62(13):1484-87.

Volkmuth, et al., "DNA Electrophoresis in Microlithographic Arrays," (1992), Nature vol. 358, pp. 600-602.

Washizu, et al., "Applications of Electrostatic Stretch-and-Positioning of DNA," (1995). IEEE Trans. Industry Applications vol. 31, pp. 447-456.

Washizu, et al., "Electrostatic Manipulation of DNA in Microfabricated Structures," (1990), IEEE Trans. Industry Applications vol. 26, pp. 1165-1172.

Wong et al., Deformation of DNA molecules by hydrodynamic focusing. J Fluid Mech. 2003;497:55-65.

Wuite et al., Single-molecule studies of the effect of template tension on T7 DNA polymerase activity. Nature. Mar. 2, 2000;404(6773):103-6.

Zimmermann, et al., "DNA Stretching on Functionalized Gold Surfaces," (1994), Nucl. Acids Res. vol. 22. pp. 492-497.

[No Author Listed] Figure 5. Physics Today Online. Available at http://www.physicstoday.org/pt/vol-54/iss-6/captions/p42cap5. html. Last accessed Jul. 15, 2002. 2 pages.

(56) References Cited

OTHER PUBLICATIONS

[No Author Listed] Fraen FLP Series Lenses for Luxeon LEDs: Luxeon I, III, and V, Star and Emitter. Jan. 4, 2005. Available at http://www.fraensrl.com/images/FLP.sub.--Lens.sub.--Series.sub.--Datashee- t.pdf. 8 pages.
Agronskaia et al. Two-color fluorescence in flow cytometry DNA sizing: Identification of single-molecule fluorescent probes. Anal. Chem. 1999;71:4684-4689. Abstract Only.
Ambrose et al., Application of single molecule detection to DNA sequencing and sizing, Ber. Bunsenges. Phys. Chem. 1993; 97:1535-1542.
Ashworth et al., Transducer mechanisms for optical biosensors. Part 2: Transducer design. Comput Methods Programs Biomed. Sep. 1989;30(1):21-31.
Austin, et al., Electrophoresis and Microlithography. Analysis. 1993; 21: 235-238.
Austin, et al., Stretch Genes. Physics Today. 1997;50:32-38.
Boone et al., Plastic advances microfluidic devices. Anal Chem. Feb. 1, 2002;74(3):78A-86A.
Burns et al., An integrated nanoliter DNA analysis device. Science. Oct. 16, 1998;282(5388):484-7. (Abstract Only).
Bustamante, et al., "Entropic Elasticity of Lambda-phage DNA," (1994), Science vol. 265, pp. 1599-1600.
Castro et al., Single-Molecule Electrophoresis: Applications to Biomolecular Detection. SPIE. 1995; 2396:79-85.
Cheek et al., Chemiluminescence detection for hybridization assays on the flow-thru chip, a three-dimensional microchannel biochip. Anal Chem. Dec. 15, 2001;73(24):5777-83.
Chen et al., Single-Molecule Detection in Capillary Electrophoresis: Molecular Shot Noise as a Fundamental Limit to Chemical Analysis. Anal. Chem. Feb. 15, 1996;68(4):690-6.
Chou, et al., "A Microfabricated Device for Sizing and Sorting DNA Molecules." (1999). Proc. Natl. Acad. Sci. USA. vol. 96, pp. 11-13.
Chu, "Laser Manipulation of Atoms and Particles," (1991), Science vol. 253, pp. 861-866.
Church et al., Multiplex DNA sequencing. Science. Apr. 8, 1988;240(4849):185-8.
Cova et al., Evolution and prospects for single-photon avalanche diodes and quenching circuits. J Mod Opt. Jun.-Jul. 2004;51(9-10):1267-88.
D'Antoni et al., Single Molecule Detection of Proteins Using Microfluidic Fluorescence Detection. ORC Poster. Apr. 2006.
Davis et al., Rapid DNA Sequencing Based on Single-Molecule Detection. Los Alamos Science. 1992; 20:280-6.
Deen, "Analysis of Transport Phenomena," (1998), Oxford University Press, NY, pp. 275-278. Abstract.
Dittrich et al., Sorting of cells and single particles in microstructures. Biophys J. 2002;82:43a. 209—Pos. Board # B70.
Duke et al., "Microfabricated Sieve for the Continuous Sorting of Macromolecules," (1998), Phys. Rev. Lett. vol. 80, pp. 1552-1555. Abstract.
Ekstrom et al., Two-point fluorescence detection and automated fraction collection applied to constant denaturant capillary electrophoresis. Biotechniques. Sep. 2000;29(3):582-4, 586-9.
Ertas, "Lateral Separation of Macromolecules and Polyelectrolytes in Microlithographic Arrays," (1998). Phys. Rev. Lett. vol. 80, pp. 1548-1551.
Fisher88, Fisher Scientific Catalog (1988) p. 861.
Foquet et al., DNA fragment sizing by single molecule detection in submicrometer-sized closed fluidic channels. Anal Chem. Mar. 15, 2002;74(6):1415-22. (Abstract Only).
Giddings et al., Chapter 1. The Field-Flow Fractionation Family: Underlying Principles. In: Field-Flow Fractionation Handbook. Wiley-Interscience. 2000: 3-30.
Goodwin et al., Spatial dependence of the optical collection efficiency in flow cytometry. Cytometry. Oct. 1, 1995;21(2):133-44.
Grandbois et al., "How Strong is a Covalent Bond?" (1999), Science vol. 283. pp. 1727-1730.
Gurrieri et al., Imaging of kinked configurations of DNA molecules undergoing orthogonal field alternating gel electrophoresis by fluorescence microscopy. Biochemistry. Apr. 3, 1990;29(13):3396-401. (Abstract Only).
Haab et al., Single molecule fluorescence burst detection of DNA fragments separated by capillary electrophoresis. Anal Chem. Sep. 15, 1995;67(18):3253-60.
Han et al., Separation of long DNA molecules in a microfabricated entropic trap array. Science. May 12, 2000;288(5468):1026-9.
Harding et al., Single-molecule detection as an approach to rapid DNA sequencing. Trends Biotechnol. Jan.-Feb. 1992;10(1-2):55-7. (Abstract).
Harrison, et al. "Capillary Electrophoresis and Sample Injection Systems Integrated on a Planar Glass Chip." (1992), Anal. Chem. vol. 64, pp. 1926-1932.
Holzwarth et al., Transient orientation of linear DNA molecules during pulsed-field gel electrophoresis. Nucleic Acids Res. Dec. 10, 1987;15(23):10031-44.
Houseal et al., "Real-time Imaging of Single DNA Molecules with Fluorescence Microscopy." (1998). Biophys. J. vol. 56, pp. 507-516.
Jacobson et al., "Fused Quartz Substrates for Microchip Electrophoresis," (1995), Anal. Chem. vol. 67, pp. 2059-2063.
Kabata, et al., "Visualization of Single Molecules of RNA Polymerase Sliding Along DNA," (1993), Science vol. 262, pp. 1561-1563.
Kartha et al., Laser-excited fluorescene of $Nd^{3+}$ in some fluoride crystals. Spectrochimica Acta Part A: Molecular Spectroscopy. 1987;43(7):911-15. Abstract Only.
Kasianowicz et al., Characterization of individual polynucleotide molecules using a membrane channel. Proc Natl Acad Sci U S A. Nov. 26, 1996;93(24):13770-3.
Kasianowicz et al., Polymer transport in the alpha-hemolysin ion channel. Page 111. Abstract 26.
Kim, et al., "Intermediates in the Folding Reactions of Small Proteins," (1990), Annu. Rev. Biochem. vol. 59, pp. 631-660.
Krogmeier et al., A Microfluidic Device for Concentrating High Molecular Weight DNA. Biophysical Society 53rd Annual Meeting. Feb. 28-Mar. 4, 2009. Boston. Poster. 1 Page.
Kumar et al., Molecular Serotyping and Sub-typing of *Salmonella* Strains by Genome Sequence Scanning Presented at the International Association for Food Protection (IAFP) Annual Meeting. Meeting. Jul. 31, 2013. Poster. 1 Page.
Kumar et al., Molecular Strain Typing of Shiga-toxigenic *E. coli* (STEC) by Genome Sequence Scanning. American Society for Microbiology General Meeting. May 20, 2013. Poster. 1 Page.
Kumar et al., Molecular Strain Typing of Shiga-toxigenic *E. coli* (STEC) by Genome Sequence Scanning. Association of Public Health Laboratories (APHL) General Meeting. Jun. 2, 2013. Poster. 1 Page.
Lee et al., Analysis of self-assembled cationic lipid-DNA gene carrier complexes using flow field-flow fractionation and light scattering. Anal Chem. Feb. 15, 2001;73(4):837-43.
Lee et al., Diffusion of a polymer chain through a thin membrane. J Phys II France, Feb. 1996; 6:195-204.
Lee et al., Laser-induced fluorescence detection of a single molecule in a capillary. Anal Chem. Dec. 1, 1994;66(23):4142-9.
Lee et al., Micro flow cytometers with buried SU-8/SOG optical waveguides. Sensors and Actuators. 2003;103:165-70.
Lee et al., Mircomachined pre-focused M x N flow switches for continuous multi-sample injection, J Micromech Microeng. 2001;11:654-661.
Li et al., Chapter 28. Protein Complexes and Lipoproteins. In: Field Flow Fractionation Handbook. Wiley-Interscience. 2000: 433-470.
Lyon et al., "Confinement and Detection of Single Molecules in Submicrometer Channels," (1997), Anal. Chem. vol. 69, pp. 3400-3405.
Malkin et al., Rapid Detection and Sub-Serotype Level Typing of Bacterial Organisms Using Optical Genome Sequence Scanning. American Society for Microbiology General Meeting. 2013. Poster. 1 Page.
Marko et al., 1995, "Stretching DNA", Macromolecules 28:8759-8770.

(56) References Cited

OTHER PUBLICATIONS

Meltzer et al., A lab-on-chip for biothreat detection using single-molecule DNA mapping. Lab Chip. Mar. 7, 2011;11(5):863-73. Epub Jan. 20, 2011. Supplemental Material Included. 16 Pages.

Meltzer, Single-molecule DNA mapping for pathogen detection. The Botulinum J. 2012;2(2):159-163.

Mollova et al., An automated sample preparation system with mini-reactor to isolate and process submegabase fragments of bacterial DNA. Anal Biochem. Aug. 15, 2009;391(2):135-43. doi:10.1016/j.ab.2009.05.008. Epub May 12, 2009. Supplemental Material Included. 23 Pages.

Nguyen et al., "Detection of Single Molecules of Phycoerythrin in Hydrodynamically Focused Flows by Laser-Induced Fluorescence", Anal. Chem., Sep. 1, 1987, pp. 2158-2161, vol. 59, No. 17.

Nie et al., Probing individual molecules with confocal fluorescence microscopy. Science. Nov. 11, 1994;266(5187):1018-21.

Parra et al., "High Resolution Visual Mapping of Stretched DNA by Fluorescent Hybridization," (1993). Nature Genet vol. 5, pp. 17-21.

Perkins et al., "Direct Observation of Tube-like Motion of a Single Polymer Chain," (1994), Science vol. 264, pp. 819-822.

Protozanova et al., Binding Specificity of Multi-Labeled PNA Probes Studied by Single Molecule Mapping. Biophysical Society 53rd Annual Meeting. Feb. 28-Mar. 4, 2009. Boston. 25a. 124—Pos. Board B3. Abstract.

Protozanova et al., Fast high-resolution mapping of long fragments of genomic DNA based on single-molecule detection. Anal Biochem. Jul. 1, 2010;402(1):83-90. Epub Mar. 20, 2010.

Protozanova et al., Fast high-resolution mapping of long fragments of genomic DNA based on single-molecule detection. Anal Biochem. Jul. 1, 2010;402(1):83-90. Epub Mar. 20, 2010. Supplemental Data. 29 Pages.

Radcliff et al., Chapter 1. Basics of flow cytometry. In: Methods Mol Biol. 1998;91:1-24.

Ramaswamy et al., Confirmation and Typing of *Salmonella* by Genome Sequence Scanning in Presumptive Positive Food Samples. International Association for Food Protection (IAFP) Annual Meeting. Jul. 30, 2013. Poster. 1 Page.

Ramaswamy et al., Rapid Strain Typing of *Salmonella* in Food in the Presence of Competing Microflora by Genome Sequence Scanning. American Society for Microbiology General Meeting. May 29, 2013. Poster. 1 Page.

Rampino et al., Apparatus for gel electrophoresis with continuous monitoring of individual DNA molecules by video epifluorescence microscopy. Anal Biochem. May 1, 1991;194(2):278-83.

Roulet et al., Fabrication of multilayer systems combining microfluidic and microoptical elements for fluorescence detection. J Micro Systms. Dec. 2001;10(4):482-91.

Roulet et al., Performance of an integrated microoptical system for fluorescence detection in microfluidic systems. Anal Chem. Jul. 15, 2002;74(14):3400-7.

Schmalzing et al., "DNA Sequencing on Microfabricated Electrophoretic Devices," (1998), Anal. Chem. vol. 70, pp. 2303-2310.

Schmalzing et al., "DNA Typing in Thirty Seconds with a Microfabricated Device," (1997), Proc. Natl. Acad. Sci. USA vol. 94, pp. 10273-10278.

Schwartz et al., "Conformational Dynamics of Individual DNA Molecules During Gel Electrophoresis," (1989), Nature vol. 338, pp. 520-522.

Schwartz et al., "Ordered Restriction Maps of *Saccharomyces cerevisiae* Chromosomes Constructed by Optical Mapping," (1993), Science vol. 262, pp. 110-114.

Seiler et al., "Planar Glass Chips for Capillary Electrophoresis: Repetitive Sample Injection, Quantitation and Separation Efficiency," (1993), Anal. Chem. vol. 65, pp. 1481-1488.

Shera et al., Detection of single fluorescent molecules. Chem Phys Letts. Nov. 23, 1990;174(6):553-7.

Shortreed et al., High-throughput single-molecule DNA screening based on electrophoresis. Anal Chem. Jul. 1, 2000;72(13):2879-85.

Smith et al., "Observation of Individual DNA Molecules Undergoing Gel Electrophoresis," (1989), Science vol. 243, pp. 203-206.

Smith et al., Molecular Engineering of the *Autographa californica* Nuclear Polyhedrosis Virus Genome: Deletion Mutations Within the Polyhedrin Gene. J Virol. May 1983;46(2):584-93.

Smith et al., Physical Analysis of *Autographa californica* Nuclear Polyhedrosis Virus Transcripts for Polyhedrin and 10,000-Molecular-Weight Protein. J Virol. Jan. 1983;45(1):215-25.

Son et al., A platform for ultrasensitive and selective multiplexed marker protein assay toward early-stage cancer diagnosis. Nanomedicine (Lond). Feb. 2007;2(1):79-82.

Soper et al., Nanoliter-scale sample preparation methods directly coupled to polymethylmethacrylate-based microchips and gel-filled capillaries for the analysis of oligonucleotides. J Chromatography A. 1999;853:107-20.

Tan et al., "Nanoscale Imaging and Sensing by Near-Field Optics, in: Fluorescence Imaging: Spectroscopy and Microscopy," (1996), Wang and Herman eds., Chem. Anal. Series vol. 137, pp. 407-475.

Thaxton et al., 19. DNA—Gold-Nanoparticle Conjugates. Nanotechnology. 2004:288-307.

Volkmuth, et al., "DNA Electrodiffusion in a 2D Array of Posts," (1994), Phys. Rev. Lett. vol. 72, pp. 2117-2120.

Wabuyele et al., Single molecule detection of double-stranded DNA in poly(methylmethacrylate) and polycarbonate microfluidic devices. Electrophoresis. Oct. 2001;22(18):3939-48. (Abstract Only).

Wahlund et al., Application of an asymmetrical flow field-flow fractionation channel to the separation and characterization of proteins, plasmids, plasmid fragments, polysaccharides and unicellular algae. J Chromatogr. Jan. 6, 1989;461:73-87.

Wang et al., High-resolution capillary array electrophoretic sizing of multiplexed short tandem repeat loci using energy-transfer fluorescent primers. Electrophoresis. 1996;17:1485-1490.

Wang et al., Rapid sizing of short tandem repeat alleles using capillary array electrophoresis and energy-transfer fluorescent primers. Anal. Chem. 1995;67:1197-203.

Watson et al., The early fluidic and optical physics of cytometry. Cytometry. Feb. 15, 1999;38(1):2-14.

White et al., *Staphylococcus aureus* strain typing by single-molecule DNA mapping in fluidic microchips with fluorescent tags. Clin Chem. Dec. 2009;55(12):2121-9. Epub Oct. 8, 2009.

White et al., *Staphylococcus aureus* strain typing by single-molecule DNA mapping in fluidic microchips with fluorescent tags. Clin Chem. Dec. 2009;55(12):2121-9. Epub Oct. 8, 2009. Supplemental Data. 22 Pages.

Whitesides et al., Flexible Methods for Microfluidics: Devices for handling nanoliter qualities of fluids are creating new fabrication challenges and finding new applications in biology, chemistry, and materials science. Physics Today Online. Jun. 2001, 8 pages.

Whitesides et al., Generating Microgradients. Harvard MRSEC—Research Nuggets. Materials Research Science and Engineering Center. Feb. 2, 2001. Available at http://www.mrsec.harvard.edu/research/nugget.sub.--4.html. Last accessed Jul. 15, 2002. 1 page.

Whitesides, Fabrication of Complex, 3D Microstructures. Harvard MRSEC—Research Nuggets. Materials Research Science and Engineering Center. Available at http://www.mrsec.harvard.edu/research/nugget.sub.--3.html. Last accessed Jul. 15, 2002. 1 page.

Whitesides, Three-Dimensional Networks of Fluid Channels in PDMS. Harvard MRSEC—Research Nuggets. Materials Research Science and Engineering Center. Jun. 1, 2000. Available at http://www.mrsec.harvard.edu/research/nugget.sub.--11.html. Last accessed Jul. 15, 2002. 1 page.

Wilding et al., Manipulation and flow of biological fluids in straight channels micromachined in silicon. Clin. Chem. 1994;40(1): 43-47. (Abstract Only).

Wong et al., Direct Manipulation of DNA Molecules Using Hydrodynamic Force. 2002 IEE International Conference on Robotics and Automation. Washington, D.C. May 12, 2002. 27 Pages.

Woolley et al., "Ultra-high Speed DNA Fragment Separations Using Microfabricated Capillary Array Electrophoresis Chips," (1994), Proc. Natl. Acad. Sci. USA vol. 91, pp. 11348-11352.

(56) References Cited

OTHER PUBLICATIONS

International Search Report and Written Opinion for PCT/US2013/037140 dated Jul. 18, 2013 and claims as filed from PCT/US2013/037140 (34 pages).

[No Author Listed] Simultaneous DNA Stretching and Intercalation in Continuous Elongational Flow. 58th Annual Meeting of the Biophysical Society, San Francisco, CA. PathoGenetix Poster Abstract. Feb. 15-19, 2014. 1 Page.

Kumar et al., Evaluation of genome sequence scanning technology for molecular (sub)-serotyping of *Salmonella* and simultaneous detection of multiple *Salmonella serovars* in complex mixtures. 4th Am Soc for Microbiol (ASM) Meeting on *Salmonella*. Oct. 9, 2013. Poster. 1 Page.

Kumar et al., Strain typing of BIG 7 STECs and differentiation from stx- and/or eae—BIG 7 serogroup *E. coli* by Genome Sequence Scanning. 114th General Meeting American Society of Microbiology, May 19, 2014. Poster. 1 Page.

Pouseele et al., An Integrated Rapid Strain Typing Solution Combined With a Polyphasic Bioinformatics Tool has the Potential to Considerably Reduce the Time for Routine Outbreak Detection. InFORM 2013: Integrated Foodborne Outbreak Response and Management Meeting. Nov. 19, 2013. Poster. 1 Page.

Protozanova et al., Rapid Molecular Serotyping of *Listeria* spp. by Genome Sequence Scanning. 114th General Meeting American Society of Microbiology, May 19, 2014. Poster. 1 Page.

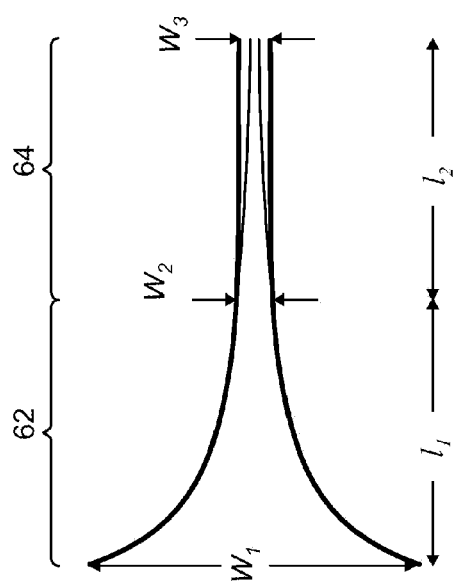
FIG. 1A
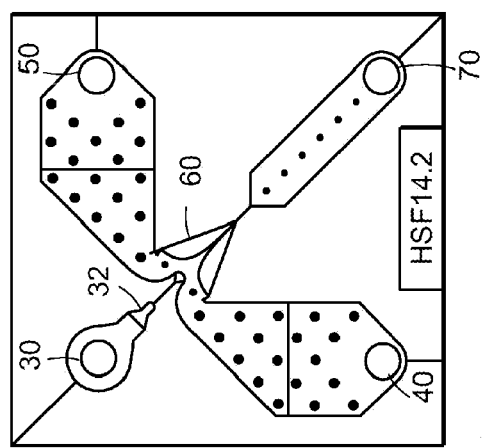
FIG. 1B
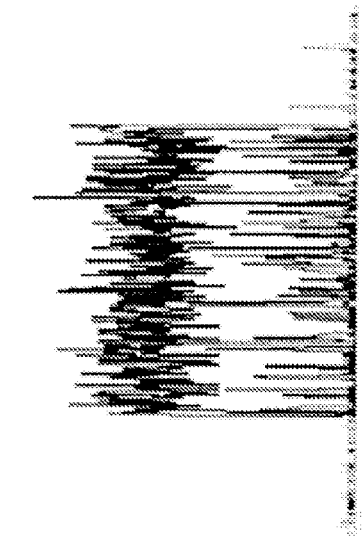
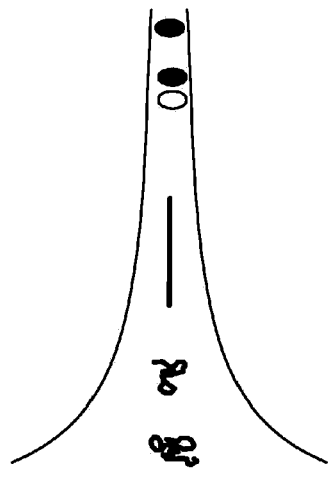
FIG. 1C
FIG. 1D

| Geometric parameters | Funnel design | | | | |
| --- | --- | --- | --- | --- | --- |
| | CV 7.5 | CV 30a | CV 30b | CS 30 | CS 50 |
| $W_1$ (μm) | 250 | 1000 | 1000 | 1000 | 1000 |
| $W_2$ (μm) | 5 | 5 | 5 | 10.2 | 11.9 |
| $W_3$ (μm) | 5 | 5 | 5 | 5 | 7.6 |
| $L_1$ (μm) | 200 | 900 | 900 | 600 | 1100 |
| $L_2$ (μm) | 200 | 350 | 350 | 350 | 350 |
| etch depth (μm) | 1 | 1 | 2 | 2 | 2 |
| $F_1$ (μm$^3$) | $2.7 \times 10^5$ | $4.7 \times 10^6$ | $4.7 \times 10^6$ | $4.5 \times 10^6$ | $1.8 \times 10^7$ |
| $F_1$ (μm$^2$) | NA | NA | NA | 3433 | 7361 |

| Geometric parameters | Funnel design | | | | |
| --- | --- | --- | --- | --- | --- |
| | CV 7.5 | CV 30a | CV 30b | CS 30 | CS 50 |
| nominal fluid velocity (μm/ms) | 7.5 | 30 | 30 | 30 | 50 |
| peak strain rate (ms$^{-1}$) | 0.063 | 0.062 | 0.062 | 0.062 | 0.065 |
| sustrained strain rate (ms$^{-1}$) | 0 | 0 | 0 | 0.062 | 0.065 |
| Stretching funnel length (μm) | 200 | 900 | 900 | 600 | 1100 |
| $F_1$ (μm$^3$) | $2.7 \times 10^5$ | $4.7 \times 10^6$ | $4.7 \times 10^6$ | $4.5 \times 10^6$ | $1.8 \times 10^7$ |
| Detection channel length (μm) | 200 | 350 | 350 | 350 | 350 |
| $F_2$ (μm$^2$) | NA | NA | NA | 3433 | 7361 |
| $X_{tag}$ (μm) | NA | NA | NA | 113.8 | 147.3 |
| etch depth (μm) | 1 | 1 | 2 | 2 | 2 |

FIG. 2

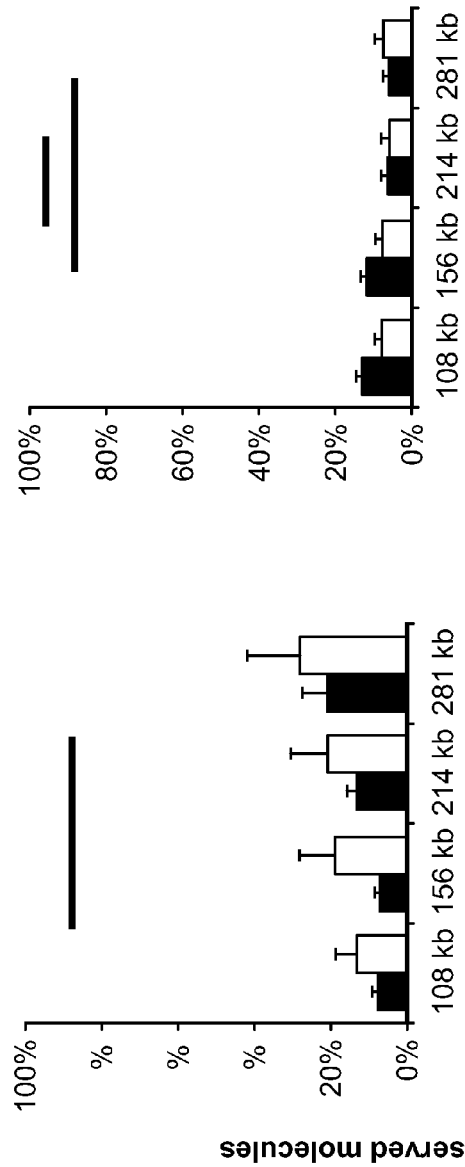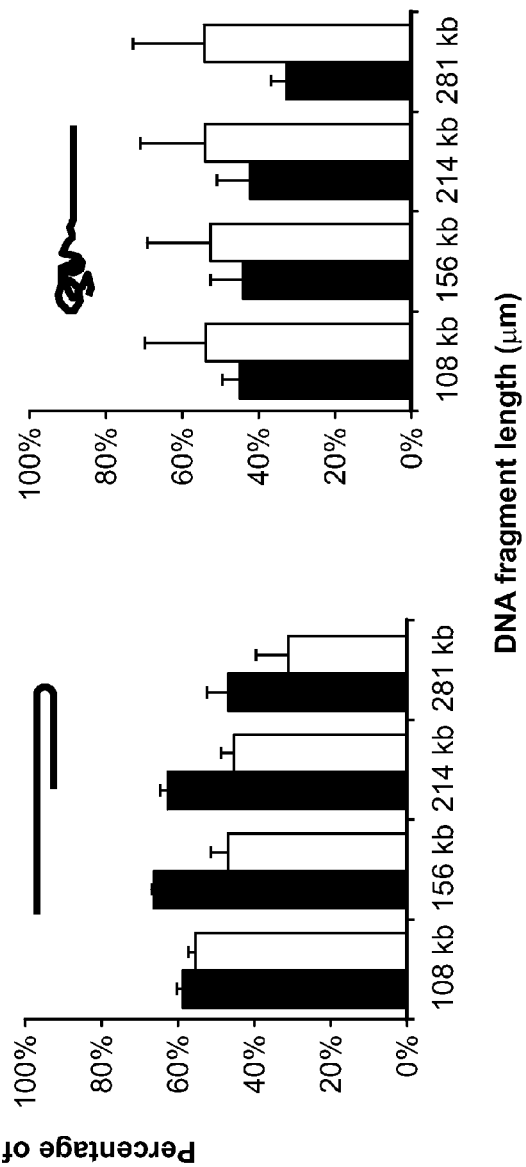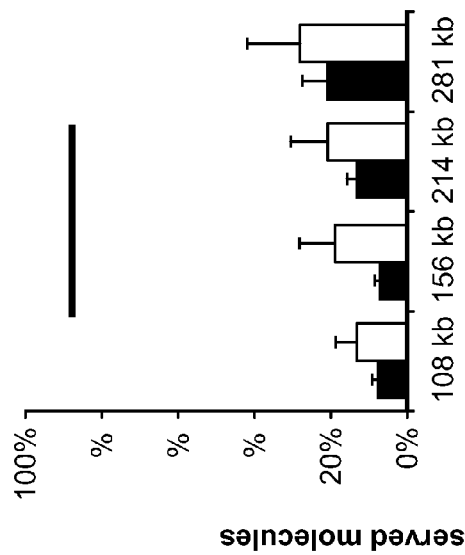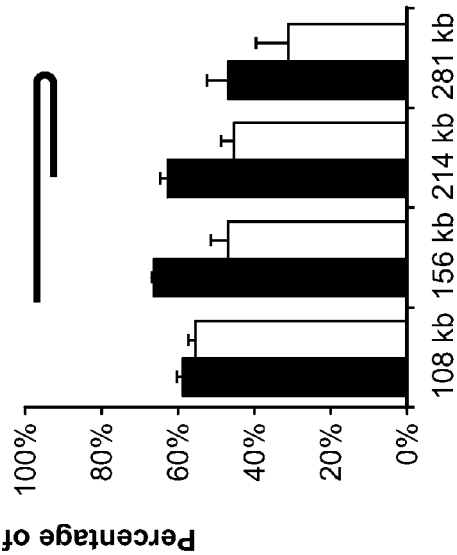

FIG. 6A
FIG. 6B
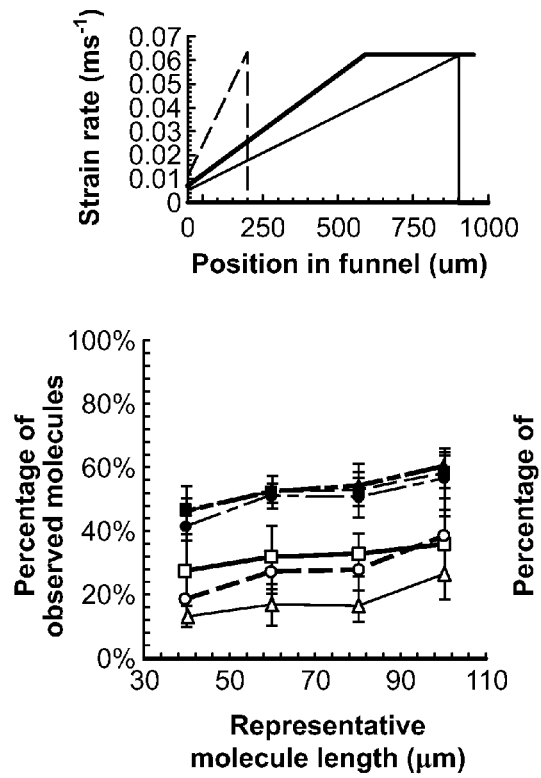
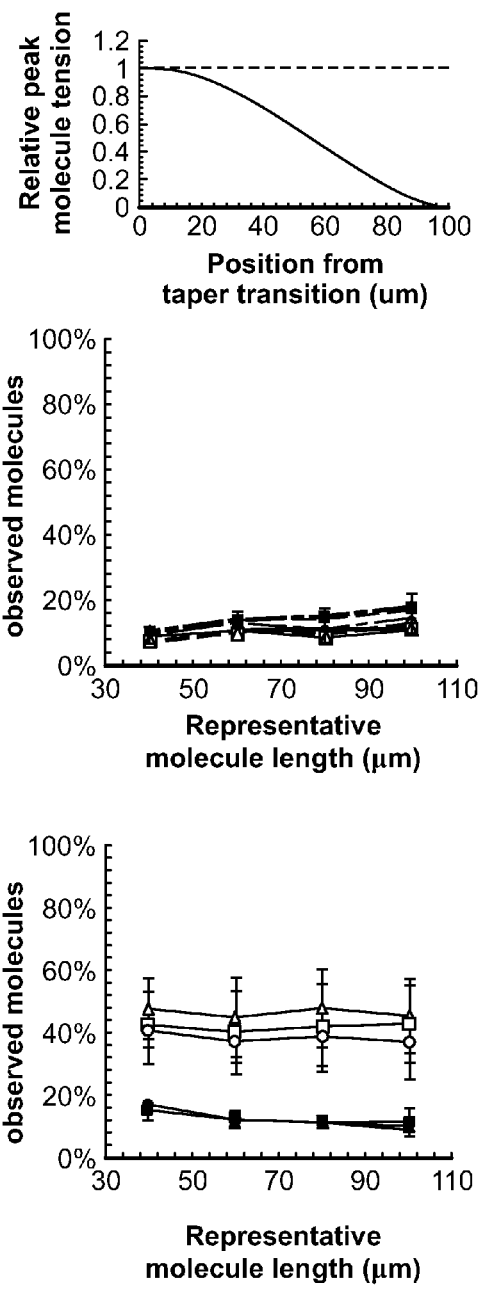

DEVICE FOR STRETCHING A POLYMER IN A FLUID SAMPLE

RELATED APPLICATIONS

This application claims the benefit under 35 U.S.C. §119 (e) of U.S. Provisional Application Ser. No. 61/625,745, entitled "DEVICE FOR STRETCHING A POLYMER IN A FLUID SAMPLE" filed on Apr. 18, 2012, and U.S. Provisional Application Ser. No. 61/784,399, entitled "DEVICE FOR STRETCHING A POLYMER IN A FLUID SAMPLE" filed on Mar. 14, 2013, the entire contents of both of which are incorporated herein by reference.

FIELD

The present invention is directed to a device for stretching at least one polymer in a fluid sample, where the device includes a tapered channel.

SUMMARY

According to one aspect, a device for stretching at least one polymer in a fluid sample is provided. The device includes an elongation structure, where said elongation structure includes a tapered channel that decreases in width from a first end to a second end. The tapered channel includes a first zone having a first tapered shape, and a second zone having a second tapered shape, where the second tapered shape is different than the first tapered shape. The at least one polymer, when present, moves along said tapered channel from said first end to said second end and is stretched. The first tapered shape may include an increasing strain rate taper, and the second tapered shape may include a constant strain rate taper.

According to another aspect, a method includes moving a polymer through a tapered channel past at least one detection station, where the tapered channel has a constant strain portion. The method also includes detecting an object-dependent impulse that conveys information about structural characteristics of the polymer, such as a nucleotide sequence or hybridization of the polymer to a sequence-specific probe, and obtaining an observed trace based on the detected impulse, where the observed trace is an intensity versus time trace. The method also includes applying an acceleration correction to the observed trace and obtaining a corrected intensity versus distance trace from the application of the acceleration correction to the observed trace.

Various embodiments of the present invention provide certain advantages. Not all embodiments of the invention share the same advantages and those that do may not share them under all circumstances.

Further features and advantages of the present invention, as well as the structure of various embodiments that incorporate aspects of the invention are described in detail below with reference to the accompanying drawings.

BRIEF DESCRIPTION OF FIGURES

The foregoing and other objects and advantages of the invention will be appreciated more fully from the following figures, wherein like reference characters designate like features, in which:

FIG. 1A is a schematic representation of a microfluidic chip with an elongation structure according to one embodiment;

FIG. 1B is a schematic representation of a tapered channel with two zones according to one embodiment;

FIG. 1C is a schematic representation of a DNA sample being stretched in a tapered channel according to one embodiment;

FIG. 1D includes representative fluorescent signals generated from a single stretched DNA molecule;

FIG. 2 includes a chart which includes data from prior art tapered funnels and also data from two embodiments of the present invention;

FIGS. 5A-5D illustrate the effect of channel depth on single molecule morphology FIGS. 6A-6B illustrate improved DNA stretching efficiency in constant strain rate detection funnels;

DETAILED DESCRIPTION OF INVENTION

Figure 3A:
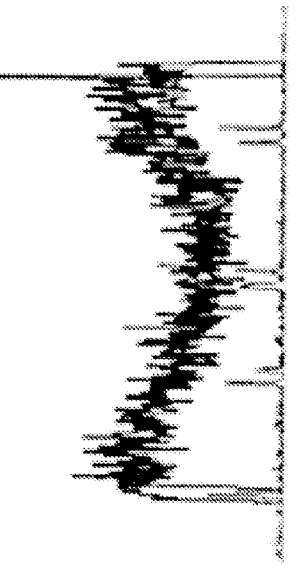
FIG. 3A is a schematic representation of a DNA sample being stretched in a tapered channel according to one embodiment.
Figure 3B:
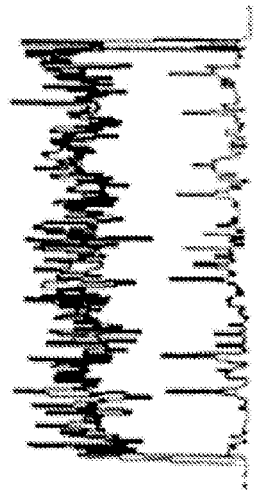
FIGS. 3B-3F represent single molecule stretching morphologies.
Figure 3C:
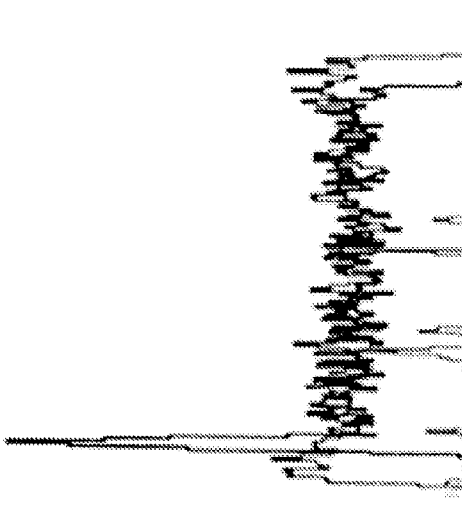
Figure 3D:
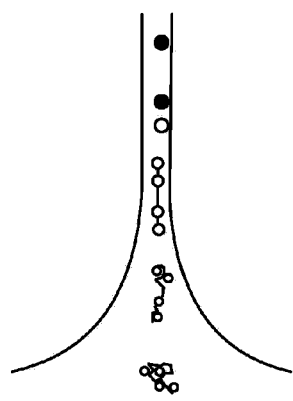
Figure 3E:
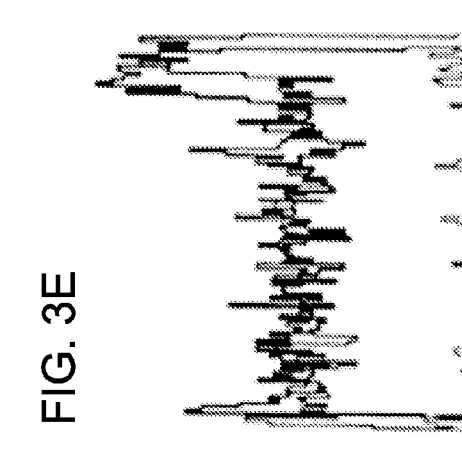
Figure 3F:
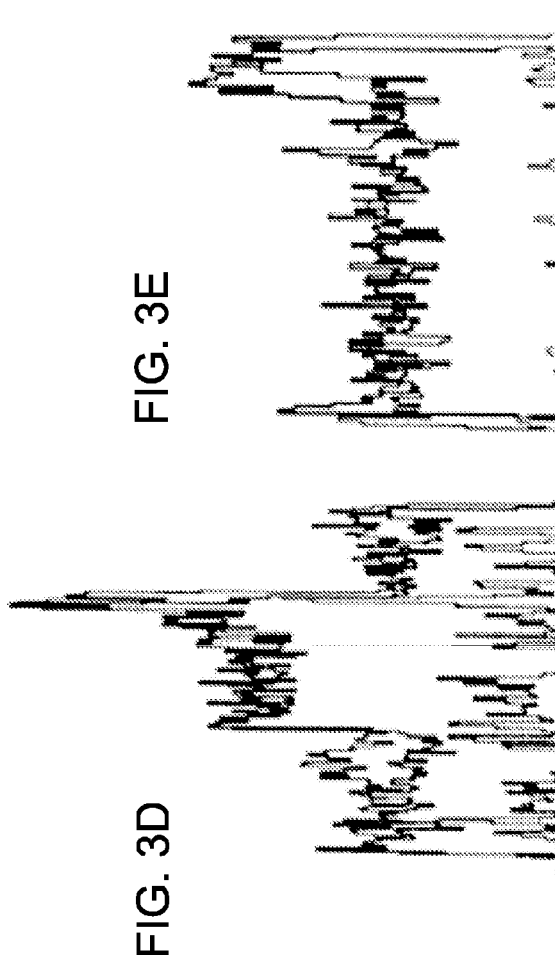

The present invention provides devices that allow polymers of any length, including nucleic acids containing entire genomes, to be stretched into a long, linear conformation for further analysis. Polymers are loaded into a device and run through the structures, propelled by, inter alia, physical, electrical or chemical forces. Stretching is achieved by, e.g., applying shear forces as the polymer passes through the device. Because the forces are applied continuously, it is possible to stretch out polymers to a length that is equal to or greater than the active area of the apparatus, i.e., where information about the polymer is collected as the polymer is analyzed. For example, if a video camera or laser illuminated volume is focused on the region of the chip where spreading occurs, unlimited lengths of DNA molecules can be monitored, i.e., much larger than the video image or the laser illumination volume. Since multiple molecules may be stretched in succession, extremely high throughput screening, e.g., screening of more than one molecule per second, may be achieved.

An extended labeled polymer may be moved past at least one detection station, at which labeled units of the polymers interact with the station to produce an object-dependent impulse. As used in this application, "moves past" refers to embodiments in which the station is stationary and the extended polymer is in motion, the station is in motion and the extended polymer is stationary, and the station and extended polymer are both in motion. As used herein, a "detection station" is a detection arrangement that detects physical quantities and/or properties of a polymer. Such properties include emission of energy or light of one or more wavelengths, wherein such emission is the result of laser interaction with the polymer or a sequence-specific probe hybridized to the polymer, including one or more fluorophores attached thereto. A detection station includes detection instruments, such as a camera, CCD camera or a silicon-intensified camera, a laser and optical detector combination, a light and optical detector combination, confocal fluorescence illumination and detection, or any other suitable detection instrument. This process is discussed in greater detail in U.S. Pat. No. 6,696,022 which is herein incorporated by reference in its entirety.

The devices of the invention are used in conjunction with methods for analyzing the extended polymers by detecting signals referred to as object-dependent impulses. An "object-dependent impulse," as used herein, is a detectable physical quantity which transmits or conveys information about the structural characteristics of at least one unit-specific marker of an extended polymer. A unit-specific marker, as used herein, can either be a measurable intrinsic property of a particular type of individual unit of the extended polymer, e.g., the distinct absorption maxima of the naturally occurring nucleobases of DNA (the polymer is intrinsically labeled), or a compound having a measurable property that is specifically associated with one or more individual units of a polymer (the polymer is extrinsically labeled). A unit-specific marker of an extrinsically labeled polymer may be a particular fluorescent dye with which all nucleobases of a particular type, e.g., all thymine nucleobases, in a DNA strand are labeled. Alternatively, a unit-specific marker of an extrinsically labeled polymer may be a fluorescently labeled oligonucleotide of defined length and sequence that hybridizes to and therefore "marks" the complementary sequence present in a target DNA. Unit-specific markers may further include, but are not limited to, sequence specific major or minor groove binders and intercalators, sequence-specific DNA or peptide binding proteins, sequence specific PNAs, etc. The detectable physical quantity may be in any form that is capable of being measured. For instance, the detectable physical quantity may be electromagnetic radiation, chemical conductance, radioactivity, etc. The object-dependent impulse may arise from energy transfer, directed excitation, quenching, changes in conductance (resistance), or any other physical changes. In one embodiment, the object-dependent impulse arises from fluorescence resonance energy transfer ("FRET") between the unit-specific marker and the station, or the environment surrounding the station. In preferred embodiments, the object-dependent impulse results from direct excitation in a confined or localized region, or epiillumination of a confocal volume or slit-based excitation is used. Possible analyses of polymers include, but are not limited to: determination of polymer length, determination of polymer sequence, determination of polymer velocity, determination of the degree of identity of two polymers, determination of characteristic patterns of unit-specific markers of a polymer to produce a "fingerprint", and characterization of a heterogeneous population of polymers using a statistical distribution of unit-specific markers within a sample population.

There are numerous methods and products available for analyzing polymers as described in PCT Publication No. WO 98/35012, which is incorporated herein by reference in its entirety.

The genetic information of all cellular and some viral organisms is encoded in long polymeric chains of DNA. The ultimate resolution of base-by-base DNA sequence is unique for each organism. The identity and interrelatedness of organisms however can be determined by lower resolution detection of repeated elements in their genetic code. Genomic technology is capable of optically characterizing the length of individual restriction endonuclease digested molecules, and identifying the spatial location of fluorescent labels tagged to repeated sequence motifs on each molecule of DNA. Genomic technology has wide ranging applicability in identification of bacterial genomic DNA.

The ability to optically resolve discrete sites of fluorescent labeling requires physical manipulation of each molecule such that it is stretched into a fully elongated, linearized conformation. Previous studies have demonstrated the efficacy of stretching long fragments of bacterial genomic DNA in microfluidic devices with combined shear and elongational flows. In two-dimensional tapered funnels etched to 1 μm depth, DNA stretching is strongly affected by the funnel taper, and confinement of the DNA to the 1 μm deep channel serves to pre-stretch the DNA, resulting in more uniform stretching. This ability to elongate single fragments of DNA in continuous flow conditions is highly advantageous over alternative DNA elongation methods because of the ease of sample manipulation, high sample throughput, and simplicity of the microfluidic device.

The sensitivity of Genomic technology as a detection and identification method is limited by DNA detection throughput, resolution of length information, and the range of fragment lengths that can be fully extended. By careful consideration of the stretching funnel geometry, Applicants have significantly improved these factors. First, as set forth below, the relationship between the effects of fluid velocity, funnel taper, and fragment length range have been correlated to allow for design of funnel geometries that stretch a desired range of fragment lengths at any desired fluid velocity. Second, as set forth below, novel funnel geometries have been designed that maintain the tension of stretched DNA molecules during detection. This increases analyzable molecule throughput by stretching a higher percentage of molecules to the fully extended state and eliminating relaxation and shear-induced molecular tumbling during detection. Finally, funnel geometries that maintain tension in the DNA detection channel dictate continuous acceleration of the molecule. Correct molecule analysis requires corrections of this acceleration. Because the acceleration profile is dictated by the funnel geometry, the acceleration correction can be determined from the funnel taper.

As set forth in greater detail in U.S. Pat. No. 6,696,022, it is generally desirable for the polymer sample to be in a stretched elongated state. However, a polymer sample is typically in a lower-energy, more coiled conformation. Therefore, aspects of the present invention are directed to devices with elongation structures that include tapered channels that are designed to stretch the polymer sample and then cause the polymer sample to remain in a stretched conformation.

As set forth in greater detail below, aspects of the present invention are directed to devices with tapered channels with at least a first zone having a first tapered shape and a second zone having a second tapered shape, where the second tapered shape is different than the first tapered shape. As discussed below, in one illustrative embodiment, the first tapered shape includes an increasing strain rate taper, and the second tapered shape includes a constant strain rate taper. The increasing strain rate taper may be configured to stretch, straighten out and/or elongate the polymer sample. The constant strain rate taper may be configured to substantially maintain the elongated shape of the polymer sample to prevent the polymer from returning to a more coiled and/or hairpin shape.

By way of background, as discussed in U.S. Pat. No. 6,696,022, a constant shear rate, or change in average velocity with distance in the channel, is defined as S:

$$\partial u/\partial x = S$$

where x is the distance down a substantially rectangular channel, and u is the average fluid velocity in the x direction, which is computed from the overall fluid flow (O) and the cross sectional area, A, of the channel as follows:

$$u = Q/A$$

In one embodiment where the channel cross-section is rectangular, the channel may be defined by a constant height, H and width, W such that the cross-sectional area A=HW, and the average fluid velocity is given by:

$$u = Q/HW$$

Applying the boundary condition that the fluid flow must be continuous (i.e., incompressible), Q is constant. Hence, u is inversely proportional to W. This relationship can be substituted into the original expression for S to determine a relationship between the shear rate and the width:

$$S = \partial u/\partial x = Q/H \, \partial/\partial x(1/W) = (-Q/HW^2)(dW/dx)$$

$$dW/dx = (-SH/Q)(W^2)$$

Integrating this expression, it is found that:

$$W = (SHx/Q + C)^{-1}$$

where C is a constant of integration determined by the original width of the channel (boundary condition). Similar calculations may readily be completed by those of skill in the art for non-rectangular channel shapes. When no net momentum transfer occurs in the height axis, i.e., when the velocity profile in the z-axis has been established, the shear rate from the width profile results in a stretching force. Illustrating in the case of a Newtonian fluid, the stress tensor, $t_{yz}$, required to compute the force is easily expressed in terms of the shear rate:

$$F = \iint -t_{yz} \, dz \, dx = \iint -\mu(du/dx) dz \, dx = \iint -\mu S \, dz \, dx$$

where μ is the solution viscosity. In these equations, x is the direction of motion, y is the width, and z is the height. The surface over which the shear rate needs to be integrated is that of the channel wall, which results in:

$$F = \mu HLS$$

where L is the length of the channel wall, approximately the length of the channel in which 15 the constant shear is maintained.

The structures for stretching DNA of the present invention ("elongation structures") comprise two components: a delivery region and a region of polymer elongation. The delivery region is a wider channel that leads into and out of the region of polymer elongation. The region of elongation comprises a tapered channel (i.e. a funnel).

Funnel structures are tapered channels that apply elongational forces in a regular and continuous manner as the polymer flows down the channel. The particular elongational forces are defined by the type of channel structure and shape. The channel may include a tapered channel that begins at a given width and continuously decreases to a second width, creating an increasing elongational force in the funnel portion of the channel defined by:

$$du/dx = (-Q/H)(dW/dx)(1/W^2)$$

In one embodiment of the invention, for at least a portion of the channel, the width of the channel decreases linearly so that dW/dx is constant; in this embodiment, the shear, du/dx, thus increases as W decreases. In this embodiment, the angle of the funnel as measured from the continuation of a straight wall is preferably between 1° and 75°, with a most preferred value of 26.6° for DNA in a low viscosity solution such as TE (10 mM TRIS, 1 mM EDTA) buffer, pH 8.0. Starting widths for the linear funnel embodiment preferably range from 1 micron to 1 cm, with ending widths preferably in the range of 1 nm to 1 mm depending on the polymer in question, and in one embodiment, values of 50 microns and 5 microns, respectively, for DNA.

In one embodiment, at least a portion of the channel may also be configured such that the width decreases at a decreasing rate as fluid passes down the channel, resulting in an increase in strain rate as the channel is traversed. Such tapers may offer especially good protection against natural relaxation of the polymer, since as time passes and the molecules move down the channel, they face increasing counter-forces to their tendency to recoil. Furthermore, the increasing force taper allows some design flexibility; any polymer that will encounter elongational forces large enough to cause the polymer to stretch in the taper and will not encounter elongational forces large enough to cause the polymer to break in the taper can be successfully run through the taper and stretched. There is no need to find the ideal or threshold force for the polymer, only an effective range. The inventors have appreciated that, in situations involving pressure driven fluid flow, increasing strain rate tapers may yield uniform and reproducible elongation compared to sudden-onset or continuous strain-rate tapers. The gradual onset of polymer deformation achieved in increasing strain rate tapers allows for more thorough sampling of conformational space for each polymer, thus avoiding trapping of molecules in partially extended states.

In one embodiment, at least a portion of the tapered channel is designed such that the strain rate is constant. The value of the constant strain rate required to achieve an adequate force to completely stretch the polymer over the course of the channel will vary based on the length of that channel.

The strain rate of the funnel can be determined by measuring the distance between two known points on a strand of DNA. For example, concatamers of λ DNA are used as standards for elongational force measurements. A unique sequence on each concatamer is fluorescently tagged with a hybridization probe. The interprobe distance on the concatamer is thus the length of a single λ DNA molecule (48 kilobases). The physical distance between the probes is determined using video microscopy or time-of-flight measurements. The physical distance for λ DNA in native solution is 14.1 This value is compared with the actual measured physical distance. For instance, if the measured distance is 15.0 μm, then the strain rate can be calculated from the amount of stretching that the DNA has experienced in the stretching structures. The predicted elongational force on the DNA, as measured by the velocity of the DNA and the dimensions of the channel, is matched with the elongation of the DNA and its intrinsic non-linear stiffness.

Now turning to the figures, as shown in FIG. 1, in one illustrative embodiment, the device 10 includes an elongation structure that is formed into a chip. As shown, the device 10 may include four ports and may include a sample loading port 30, two sheath buffer channels 40, 50, the elongation structure 60 (may also be called the DNA stretching funnel), and a waste port 70. As illustrated, in one embodiment, there is a delivery channel 32 between the sample loading port 30 and the elongation structure, and there are two opposing buffer channels 40, 50 that also lead into the elongation structure.

The DNA stretching funnel 60 geometry was optimized based upon experimental results. In one illustrative embodiment, the structure of the funnel 60 is divided into two distinct regions or zones. The first zone 62 may be defined as the stretching portion of the funnel, and the second zone 64 may be defined as the detection region. The first zone 62 may have a first tapered shape, and the second zone 64 may have a second tapered shape, different from the first zone. Distinct taper definitions may be required for each region. The overall funnel geometry may therefore be fully described by three characteristic widths ($w_1$=width of first end of tapered channel, $w_2$=width of tapered channel at transition between first zone 62 and second zone 64, and $w_3$=width of tapered channel at the second end of the tapered channel), two characteristic lengths ($l_1$=length of first zone, and $l_2$=length of second zone), and two taper definition equations. These geometries are detailed in FIG. 1B.

Previous studies have demonstrated that DNA stretching is most uniform when the initial DNA extension occurs gradually in an increasing-strain rate funnel. In some embodiments, the geometry of the first zone 62 (the stretching portion) of the funnel may be described by the following equations:

$$w(x) = \frac{1}{(bx+c)^2} \quad \text{Equation 1}$$
$$b = \frac{1}{l_1}\left(\sqrt{1/w_2} - \sqrt{1/w_1}\right)$$
$$c = \sqrt{1/w_1}$$

Where the width of the channel (w(x)) is a function of the distance along the funnel ($l_1$), the initial funnel width ($w_1$) and the width at the transition between the stretching and detection portions of the funnel ($w_2$).

In some embodiments, the geometry of the first zone 62 of the funnel may be described by the following equations:

$$w(x) = \frac{2w_i v_i}{\alpha x^2} = \frac{F_1}{x^2} \quad \text{Equation 2}$$
$$F_1 = \frac{2v_x w_x x}{\dot{\varepsilon}_x}$$

Where the width of the channel w(x) is a function of the distance along the detection channel (x), the width at arbitrary position i ($w_i$), and the fluid velocity at arbitrary position i ($v_i$). $F_1$, which describes the geometrical taper coefficient for an increasing strain rate funnel, is a function of the at distance x ($v_x$), the funnel width at distance x ($w_x$), and the strain rate at distance x ($\dot{\varepsilon}_x$). The funnel taper geometry can be solved to provide a desired strain rate at any given fluid velocity.

Previously described DNA stretching funnels utilized a parallel walled detection channel, which imposed a constant-velocity fluid profile in this region. For such funnels, $w_3 = w_2$. This type of second zone 64 configuration is illustrated in FIG. 1B. In one experimental study, a novel detection channel geometry was also investigated, in which the increasing strain rate funnel transitions smoothly into a tapered detection channel with a constant-strain rate taper. This unique second zone 64 tapered configuration is also illustrated in FIG. 1B. In some embodiments, the geometry of the second zone 64 (the detection region) of the funnel may be described by the following equations:

$$w(x) = \frac{w_2}{1 + \frac{x}{a}} \quad \text{Equation 3}$$
$$a = \frac{l_2}{\frac{w_2}{w_3} - 1}$$

Where the width of the channel w(x) is a function of the distance along the detection channel (x), the width at the interface with the stretching portion of the funnel ($w_2$), and the final funnel width ($w_3$).

In some embodiments, the geometry of the second zone 64 of the funnel may be described by the following equations:

$$w(x) = \frac{F_2}{x} \quad \text{Equation 4}$$
$$F_2 = \frac{v_x w_x}{\dot{\varepsilon}}$$

Where the width of the channel w(x) is a function of the distance along the detection channel (x) and the constant strain rate taper coefficient $F_2$. $F_2$ is a function of the fluid velocity at distance x ($v_x$), the funnel width at distance x ($w_x$), and the strain rate ($\dot{\varepsilon}_x$).

FIG. 1C illustrates a DNA sample passing through the elongation structure 60 and being stretched in the tapered channel. Several funnel profiles were investigated to determine the effects of geometry on DNA extension under multiple operating conditions. The tested funnel parameters are summarized in FIG. 2.

In one embodiment, sheathing buffer flows were used to constrain the DNA stream to the center of the stretching funnel. A fluidic circuit model was used to design the dimensions of resistive elements in the microfluidic structure. The driving constraint was to normalize the width of the DNA stream at the nominal point of detection to 0.25 μm. This served multiple purposes; the DNA stream could precisely be targeted to the projected laser points in the detection channel, and all DNA molecules were subjected to a uniform flow stream in the center of the funnel, thus avoiding variations in velocity and fluidic path length near the outer walls of the funnel. Operational parameters for tested devices, including predicted driving pressures and bulk flow through the DNA injector path were derived from the fluidic models.

The microfluidic chips were fabricated by Micralyne Inc. (Edmonton, Alberta, Canada). All channels were etched in 500 μm thick fused silica to a depth of 1 or 2 μm by reactive ion etching. Through holes for fluidic access were machined by ultrasonic drilling and channels were sealed by fusion bonding to a 170 μm thick cover wafer. The finished wafers were then diced to form individual devices.

Each chip to be tested was bonded to a custom acrylic manifold (Connecticut Plastics, Wallingford, Conn.) using UV-curable adhesive (Dymax 140M, Dymax Corporation, Torrington, Conn.). To prepare chips for use, the devices were first wetted with 100 mM NaOH to remove any residual debris or surface contamination from the fluidic channels. The chips were subsequently flushed with water and TE buffers prior to use. All solutions presented to the microfluidic devices were passed through a 0.2 μm syringe filters (Millipore, Billerica, Mass.) prior to use.

A DNA sample, *Escherichia coli* K12 (MG1655) was purchased from ATCC (American Type Culture Collection, Manassas, Va.). Bacterial genomic DNA was prepared in a mini-reactor as described previously. The purified genomic DNA was restriction digested using NotI enzyme, and tagged with fluorescent labeled bis-PNA tags. The prepared DNA sample was eluted at ~0.5-1.5 ng/μl.

Immediately prior to stretching on the microfluidic device 10, a 10 μl aliquot of DNA was gently mixed with POPO-1 intercalator (Life Technologies, Grand Island, N.Y.) to uniformly stain the DNA backbone. Sample concentration was quantified by ethidium bromide-stained gel prior to intercalation in order to standardize a ratio of three nucleic acid base pairs per dye. The extent to which a given fragment of DNA is stretched in the microfluidic funnel may depend on the ratio of dye to DNA, therefore for all comparisons presented in one experiment were performed such that a common stock of intercalated DNA was used for each experiment set.

Single-molecule data acquisition was performed as previously described. A 5 μl sample of prepared, intercalated DNA was pipetted into the sample port 30 on a device 10 to be tested (see FIG. 1A). The loaded sample concentration typically varied from 0.5-1.5 ng/μl DNA. The chip was then mounted to a custom confocal fluorescence microscope. Three laser detection points were projected into the detection channel of the device. Two 455 nm spots elicited fluorescence from the POPO-1 stained DNA backbone. These spots were separated by 20 μm along the detection channel. A third detection point at 532 nm excited ATTO dyes attached to sequence specific probes. This detection point was fixed at 5 μm before the first of the 455 nm points. Fluorescence emission was collected in three discrete channels using a 100× oil-immersion microscope objective. Fluorescence signals were spectrally separated using a multi-pass dichroic element, and the individual fluorescence signals were collected through fiber coupled avalanche photodiodes (APDs, Perkin Elmer). For all experiments, data acquisition was normalized to 2 bins per micron. Spatial resolution between neighboring fluorescent events was therefore maintained regardless of the fluid velocity within the detection channel (see FIG. 2).

All data analysis was performed using custom software developed at PathoGenetix. Collation of DNA backbone and tag fluorescence signals was performed using a first software application. Clustering of molecules based on the sequence-specific tags was performed using a second software application. An example of a "tag" is a sequence-specific nucleic acid probe. Single molecule backbone fluorescence morphology was analyzed using a scripted program. This program was used to detect the incidence of elevated fluorescence along the POPO-intercalated DNA backbone. An event was defined by 3 or more consecutive bins with a fluorescence intensity greater than 1.5 times the average backbone fluorescence. Molecules with detected elevated events were characterized by the location of the event along the trace. Events could occur at the leading edge of the molecule, at the trailing edge of the molecule, or located within the length of the molecule. These events were categorized as hairpin, relaxation, or overlap events, respectively.

Detection sensitivity in genomic technology devices can be directly correlated to the detection throughput of well stretched, analyzable molecules. The first variable addressed to improve detection throughput was to simply increase the driving fluid velocity of the detection funnel. The influence of funnel geometry must be considered when changing the driving velocity in genomic technology devices.

The primary attribute affecting the extension of DNA in genomic technology funnels is the strain rate of the accelerating fluid that surrounds the DNA. The strain rate ($\epsilon$) is defined by the change in fluid velocity over a given distance along the axis of the funnel:

$$\epsilon = dV/dx \qquad \text{Equation 5}$$

Where the velocity scales inversely with the width of the funnel $$V_x = V_0 \frac{w_0}{w_x} \qquad \text{Equation 6}$$

Figure 4A:
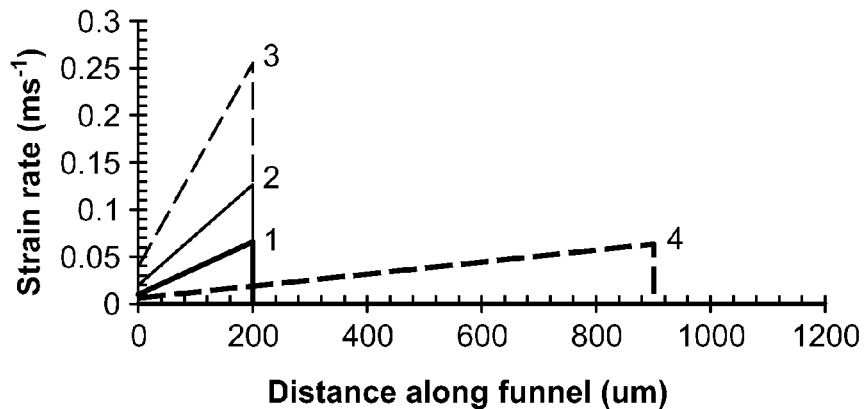
FIGS. 4A-4C illustrate molecule extension in increasing fluid velocity.

For a given funnel geometry, as the final velocity at the exit of the funnel is increased, the peak strain rate also increases proportionally (FIG. 4A). As shown in FIG. 2, a CV 7.5 funnel (constant velocity funnel) driven at 7.5 μm/ms achieves a peak strain rate of 5 μs$^{-1}$. This value increases to 10 and 20 μs$^{-1}$ at 15 and 30 μm/ms respectively. This directly impacts the peak tension experienced by a given DNA fragment, and therefore limits the range of well stretched molecules that can be achieved.

The peak tension on a single elongated molecule of DNA ($T_{max}$) can be predicted by:

$$T_{max} = \frac{\zeta_{\parallel}}{8} \times L_{mol}^2 \langle \dot{\epsilon}_{\parallel} \rangle \qquad \text{Equation 7}$$

Where $\zeta_{\parallel}$ is the parallel drag coefficient (also known as the molecular drag coefficient), $L_{mol}$ is the extended length of the molecule in microns, and $\langle \dot{\epsilon}_{\parallel} \rangle$ is the average strain rate of the funnel device, defined by:

$$\langle \dot{\epsilon} \rangle = \frac{\Delta v}{\Delta x} = \frac{v_f - v_i}{L_f} \qquad \text{Equation 8}$$

Where v is the fluid velocity at the entrance (i) or exit (f) of a funnel of length (L). $\zeta_{\parallel}$ has been previously estimated in computational models to be 0.61 centiPoise (cP). Using this value, the peak tension was calculated for all molecule lengths up to 200 um in constant velocity detection funnels (CV7.5). As the fluid velocity increased from 7.5 um/ms to 15 and 30 um/ms, the peak tension on a molecule of a given length increased dramatically. The inventors predict that an 80 μm fragment would be well stretched at 7.5 μm/ms (35 pN tension), but would overstretch dramatically at 30 μm/ms (141 pN).

Figure 4B:
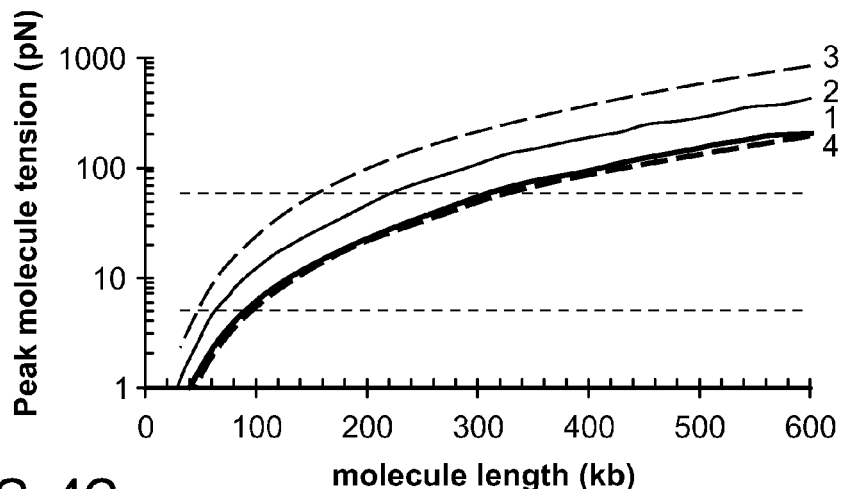
Figure 4C:
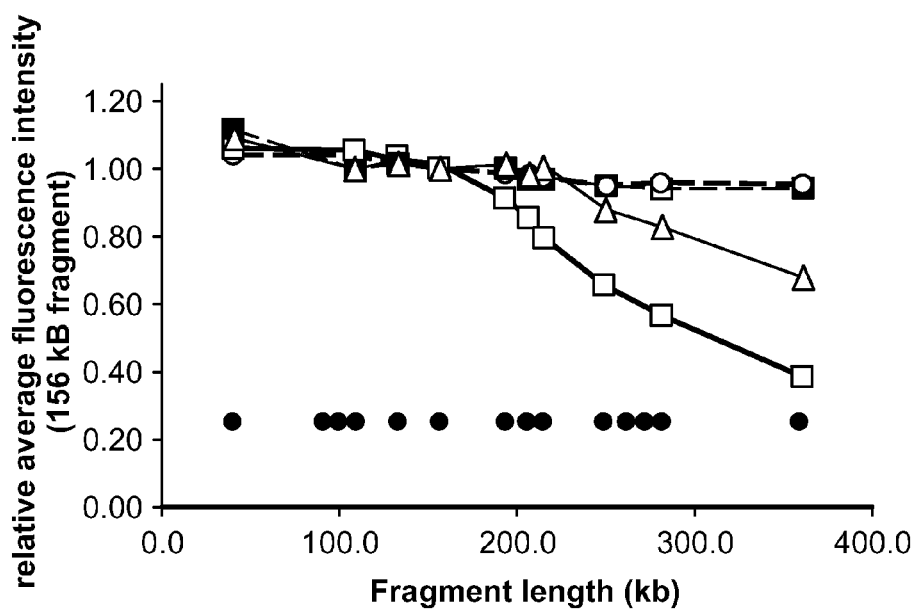

The relationships between fluid velocity, strain rate, tension, and molecule extension in the CV7.5 funnel are demonstrated in FIG. 4. A sample of *E. coli* genomic DNA digested with NotI was prepared as described above and was loaded to the CV7.5 device. Molecule stretching data was acquired at fluid velocities of 7.5, 15, and 30 μm/ms. At 7.5 μm/ms, DNA fragments ranging from 40-100 μm in length appear to be well stretched—fragments appear as discrete bursts with uniform average backbone fluorescence intensity. Molecules shorter than 40 μm appear under stretched, with a distribution of higher average fluorescence intensities. Molecules longer than 100 μm (the 358 and 361 kb fragments predicted in this digest) appear to have somewhat lower average backbone fluorescence, indicating the onset of overstretching.

At 15 and 30 μm/ms fluid velocities, the fragment distribution appears to shift. Short fragments appear to stretch to the same observed length, but longer fragments are significantly overstretched as peak tension overcomes the 60 pN threshold. The range of well-stretched fragment lengths is obviously compromised by simply increasing the driving velocity in a fixed funnel geometry.

The inventors predicted from equations 7 and 8 that the average strain rate, and therefore tension on a molecule would scale inversely with the length of the funnel—At a fixed fluid velocity, a longer funnel would produce less tension on a molecule. This effect is demonstrated in computational models in FIG. 4. The same *E. coli* digest was run on the CV 30 device (constant velocity device) at 30 μm/ms, demonstrating a similar DNA stretching pattern as observed at 7.5 μm/ms in the CV7.5 device. DNA throughput in stretching funnels can therefore be increased without loss of long, analyzable fragments if the length of the funnel is adjusted to achieve a consistent strain rate.

As demonstrated above, longer stretching funnels may be required to accommodate high fluid velocities in genomic technology devices. This poses a technical difficulty in that the fluidic resistance ($R_h$) of the microchannel scales with the length of the funnel. Reducing the geometry to the simple case of a rectangular straight channel, $$R_h = \frac{12 \, \mu L}{wh^3\left(1 - \frac{0.630h}{w}\right)} \quad \text{Equation 9}$$

Where $\mu$ is fluid viscosity, and L, w, and h are the length, width, and height of the channel respectively. Because the microfluidic device 10 may be driven by applying vacuum at the DNA waste port 70, the device 10 may be limited to a 1 atmosphere pressure drop along the channel. In a 1 µm deep device, this may imposes a constraint on the maximum channel length, fluid strain, and fluid velocity. To achieve higher fluid velocities in longer stretching funnels, the inventors explored devices with differing etch depths.

The interaction of the channel floor and ceiling may have complex effects on the stretching of DNA in fluidic devices. Constraining the coiled, unstretched DNA into the narrow confines of a 1 µm channel serves to pre-extend the DNA, due to shear interactions caused by poiseuille flow in the channel. Once extended, the rate of DNA relaxation back to the condensed state is also slowed in shallow channels. Conversely, flow in high-shear structures can lead to decreased stretching efficiency due to imposed molecular tumbling. Channel etch depth may therefore have beneficial and adverse effects that must be balanced in the design of a DNA stretching device.

To determine the effects of channel etch depth on high fluid velocity DNA stretching, the inventors compared two constant-velocity funnels designed for optimal stretching at 30 µm/ms (CV30a, CV30b, FIG. 2). The optimal fluid velocity was achieved at 25 psi in the 1 µm funnel, but at 7 psi in the 2 µm funnel. Again, the *E. coli* NotI digest was processed on both devices. The confocal laser spots were positioned 50 µm from the onset of the constant velocity zone. Roughly equivalent DNA stretching was observed on both devices—well resolved comet plots were achieved without evidence of DNA overstretching (FIG. 4). To determine subtle effects on a molecule-by-molecule basis, the inventors utilized the software algorithm described above to determine if each molecule in a given selection was well stretched, or if there was evidence of additional fluorescent signal at the leading edge, trailing edge, or middle of the molecule, thus indicating hairpinning, relaxation, or molecule overlap respectively. The inventors individually isolated clusters of molecules at ~40, 60, 80, and 100 µm in three discreet paired experiments for both the 1 µm and 2 µm deep devices.

In both devices, the efficiency of observing well-stretched molecules increased with the length of the molecule. The 2 µm deep device may appear to be more efficient in delivering well stretched DNA, across all lengths. The incidence of overlapping molecules was essentially equivalent in both devices, indicating that the molecular occupancy in the detector was uniformly low in all experiments. The 1 µm deep device caused significantly more molecules to display elevated fluorescence in the leading edge of the molecule, indicating that molecular tumbling was enhanced in the higher-shear 1 µm channel. The 2 µm channel however showed uniformly higher (although not statistically significant) incidence of elevated fluorescence in the trailing molecule edge, suggesting more rapid relaxation of molecules in the deeper channels.

In summary, retention of well stretched molecules in the 2 µm channels was no worse than observed in the 1 µm channels. Because of the benefit of being able to operate devices at lower vacuum pressures, further experiments with high velocity funnels were performed in 2 µm deep devices. These observations helped explain the complex effect of shear flow on the observation of DNA stretching. The inventors observed that stretching of DNA is substantially uniform across a long range of molecule lengths as controlled by the elongational flow established by the stretching funnel geometry. Many potentially analyzable molecules must be rejected from further analysis, however due to hairpinned or relaxed conformational states, both of which are influenced by shear flow.

While modeling strain rate as a function of the distance along the stretching funnel, the inventors note that once a molecule passes from the increasing strain region (i.e. the first zone 62) of the funnel into the constant velocity detection zone (i.e. the second zone 64, or the constant strain rate region) the fluid strain rate drops to zero, which suggests that tension along the molecule also decreases. In prior publications, the inventors have explored different stretching funnel geometries, and determined that an increasing strain rate profile yielded more uniform DNA stretching than did a funnel with constant strain rate. The inventors decided to test whether the combination of an increasing strain rate stretching funnel with a constant strain rate detection zone could improve stretching efficiencies by maintaining tension on each molecule during detection. This may be known as a compound constant strain rate funnel and data for such a device is shown in the last two columns in FIG. 2. The funnel taper profile for this detection region is described above, and the resulting strain rate profiles for 30 µm/ms constant velocity and constant strain rate funnels are shown in FIG. 4.

The relative tension profile along a molecule experiencing extensional flow may be modeled with a known funnel taper, assuming the DNA molecule is a rigid rod with a known length. The velocity of the molecule at any given position within the funnel is the average of the fluid velocity at every point along the extended molecule. In accelerating flow, the head of the molecule is therefore moving more slowly than the surrounding fluid, while the tail of the molecule moves more quickly than the surrounding fluid. The drag of the surrounding fluid elements therefore exerts tension on the molecule. The magnitude of that tension at any point along the molecule is proportional to the integral of the difference between the molecule velocity and the fluid velocity along the length of the molecule.

The inventors computed the relative tension profile on a 100 µm long molecule positioned with the head of the molecule at the origin of the constant velocity region, as well as 50 and 100 microns within the channel. At the 0 µm position, the molecule is fully constrained by the increasing strain rate region of the funnel, and displays a nearly parabolic tension profile. As the molecule precedes 50 µm along the detection zone, the inventors appreciate that the tension profile has shifted towards the tail of the molecule and the overall tension has dropped significantly. With the head of the molecule at 100 µm, it is fully within the constant velocity zone. At this point, the molecule as a whole travels at the surrounding fluid velocity and tension along the molecule has reduced to zero. From these observations, the inventors note that every molecule analyzed in a constant velocity detection zone is subjected to a complex, dynamic cycle of stretching and relaxation. The state of stretching and relaxation is also highly sensitive to the positioning of the detection point within the constant velocity zone.

By comparison, a similar model was built for a funnel comprising the increasing strain rate stretching region (i.e. the first zone 62) with the constant strain rate detection zone (i.e. the second zone 64). For this design, the inventors defined the desired point of detection to be 150 µm from the transition between the two taper profiles. The overall length of the detection zone (i.e. the second zone 64) was defined to be approximately 350 µm. Molecules up to 150 µm in length would therefore be fully constrained within the constant strain rate region (i.e. the second zone 64) of the funnel during the entire detection process. The computational model of this funnel design yields a truly parabolic tension distribution that is identical regardless of position varying 50 µm in either direction from the nominal detection point. This suggests that a DNA molecule will experience constant tension during the entire detection process.

As an initial observation, the *E. coli* NotI digest was run on the CV30 and CS30 devices (FIG. 6). The detection point was set at the 50 µm position on the CV30 device and the 150 µm position on CS30. Again, at first inspection of the comet plots, both devices provide excellent stretching of DNA, and all predicted fragment lengths were detected without obvious overstretching. Both data sets were processed through backbone filters, and the inventors recognize that the percentage of well stretched fragments was greater through all observed molecule clusters in the constant strain rate funnel as compared to the constant velocity funnel.

To further characterize the improvement in DNA stretching in constant strain rate detection channels, the inventors repeated the stretching comparisons in CV30 and CS30 devices while varying the detector spot position up to 100 µm in each device. The CV30 funnel was run at 0, 50, and 100 µm from the onset of the constant velocity region. The CS30 funnel was run with the detection point at 100, 150, and 200 µm from the transition from increasing strain rate to constant strain rate tapers. Both devices were run at fixed vacuum to achieve 30 µm/ms at 0 µm and 150 µm spot positions respectively. All data sets were again process through the software to tabulate the different mechanisms by which individual molecules would fail backbone fluorescence intensity filtration.

A significant improvement in the percentage of well-stretched molecules was detected in CS30 (constant strain funnel) compared to CV30 (constant velocity funnel). In both devices, the percentage of good molecules increased with molecule length, due to increased peak tension on longer molecules. The percentage of good molecules was uniform regardless of spot position for each isolated collection of molecule lengths. This is in stark contrast to what is observed in the CV funnel. There, we observed that more molecules pass backbone intensity filters when the spot position is at 0 µm, and decreases with the distance from the origin. The inventors also observed that the intra-experimental reproducibility in the percentage of well stretched molecules was substantially improved in the CS funnel compared to the CV funnel. The frequency of overlapped molecules again was uniformly low in all samples, indicating that the sample concentration was well-controlled for all experiments.

The percentage of molecules exhibiting hair pinned or relaxed morphologies dramatically demonstrated the difference in stretching in CS (constant strain) and CV (constant velocity) funnels. In the CS30 funnel, molecules tended to have fewer observed hairpins with increasing molecule length. The percentage of observed hair pins was independent of spot position. In the CV funnel, however, there was a significant dependence of the number of observed hair pins on the detection point in the funnel. For example, for an 80 µm fragment, only ~30% had hairpinned conformations when the detection point was at the origin of the constant velocity channel, but this increased to nearly 60% when the detection point was shifted 100 µm down the channel. This indicates that as molecules are allowed longer time in the constant velocity, no-tension portion of the channel, there is increased opportunity for shear-induced tumbling of the leading end of the molecule. This effect was eliminated in the constant strain rate funnel shown in FIG. 1B. The remaining hairpinned molecules likely represent the percentage of molecules that are not provided sufficient cumulative strain to resolve complex initial conformations—these molecules are likely never fully extended in the first place.

The CV30 funnel (constant strain funnel) also produced a uniformly high incidence of molecules exhibiting high fluorescence on the trailing edge. The number of observed relaxed molecules was highly variable form run to run, but appeared more pronounced with the spot position 100 µm from the onset of the constant velocity zone. Relaxed molecules was nearly eliminated in the CS funnel, as would be expected if the molecules were held under constant tension.

In total, use of the CS funnel (shown in FIG. 1B) as opposed to the prior art CV funnel at a given fluid velocity results in nearly two-fold improvement in the recovery of well-stretched, analyzable molecules by eliminating shear-induced molecular tumbling and relaxation.

Acceleration Correction in Constant Strain Rate Detection Channels

One ramification of detecting stretched DNA molecules in constant-tension conditions is that the molecules are continuously accelerating during the time of observation. In genomic analysis, DNA molecules are stretched to reveal the locations of sequence-specific fluorescent probes. For accelerating molecules, the spatial resolution between closely located probes will be greater at the leading end than the trailing end, due to the decreasing residence time for each segment of DNA at the detection spot. This imposes an acceleration-dependent bias on the optical signal generated from each molecule.

The detection channel may include multiple detection points. In some embodiments, the detection channel includes two backbone spots that are spaced from one another along the detection channel. The backbone spots detect fluorescence from the intercalator fluorophore. The detection channel also includes two tag spots that are spaced from one another along the detection channel. The tag spots detect fluorescence from the fluorescently labeled tags. The spatial distance between the two backbone spots is fixed and known, as is the spatial distance between the two tag spots. The position of the first backbone spot determines the position of the remaining spots within the detection channel. Each spot could be a laser spot or any other suitable detection arrangement. It should be appreciated that any number of backbone spots and/or tag spots may be used, as this aspect is not so limited.

The constant-strain detection channel geometry retains molecules under constant tension with a well-defined acceleration. The form of this acceleration can be derived analytically from the funnel geometry. Obtaining this acceleration may be critical to two related stages of data processing. In the first stage (position acceleration correction), the time and position dependence of the acceleration can be used to determine the entrance and exit time of the molecule in the tag spot, based on the entrance and exit time of the molecule in the backbone spots. In the subsequent stage (trace acceleration correction), the time dependence of the acceleration can also be used to convert the fluorescence pattern from the time domain in which it is acquired to the positional domain along the molecule. The "time domain" is also referred to herein as the intensity versus time trace or the observed trace. The "positional domain along the molecule" is also referred to herein as the distance domain or the intensity versus distance trace. The acceleration correction is used to properly convert the intensity versus time trace that was obtained during detection into an intensity versus distance trace by shifting each data point in the observed trace by an acceleration correction.

An approximation of the exact acceleration correction $\Delta x_c$ is given by:

$$\Delta x_c \cong -\frac{L^2}{2x_{tag}}\tau(1-\tau) \qquad \text{Equation 10}$$

Where $\Delta x_c$ is the difference in the distance a molecule would travel assuming a constant velocity compared to the distance traveled in the accelerating flow in the tapered channel. L is the length of the molecule. $x_{tag}$ is a funnel-geometry derived parameter, and is the distance of the point of detection from the theoretical asymptotic origin of the constant strain portion of the channel. The length of the molecule L is measured from observations of the intercalator backbone signal. The velocity of the molecule is estimated from the time-of-flight of the intercalator signal from the first backbone spot to the second backbone spot. This estimated velocity of the molecule, along with a measured dwell time in the first backbone spot, is then used to calculate the length of the molecule L. This calculated length L approximates the actual length of the molecule, as it corrects any acceleration-dependent bias. $x_{tag}$ values for the CS30 and CS50 devices are presented in FIG. 2.

$\tau$ is the time for the passage of the molecule through a detection spot. In some embodiments, the detection spot may be one of the tag spots. $\tau=0$ corresponds to the time at which the leading end of the molecule enters the detection spot. $\tau=1$ corresponds to the time at which the trailing end of the molecule leaves the detection spot. Values of $\tau$ between 0 and 1 correspond to the times at which the remaining portions of the molecule between the leading end and the trailing end enter the detection spot. For example, a value of $\tau=0.1$ may correspond to the time at which a portion of the molecule that is located behind the leading end of the molecule enters the detection spot, and a value of $\tau=0.2$ corresponds to the time at which another portion of the molecule that is located even further behind the leading end of the molecule enters the detection spot.

As such, each intensity data point plotted in the observed intensity versus time trace receives a unique $\tau$ value ranging from 0 to 1, inclusive. Because the acceleration correction is a function of $\tau$, the value of the acceleration correction will differ among the data points in the observed trace. Thus, when the acceleration correction is applied to the observed trace, each data point in the observed trace will shift by an amount that depends on the acceleration correction value that is associated with that specific data point. For example, the intensity point associated with $\tau=0$ will not shift at all, since the value of the acceleration correction at $\tau=0$ is 0. Similarly, the intensity point associated with $\tau=1$ also will not shift, since the value of the acceleration correction at $\tau=1$ is also 0. Finally, the maximum value (amplitude) of the acceleration correction $\Delta x_{cmax}$ occurs at $\tau=\frac{1}{2}$, as shown in Equation 11 below.

$$\Delta x_{cmax} \cong -\frac{L^2}{8x_{tag}} \qquad \text{Equation 11}$$

Thus, the intensity point associated with $\tau=\frac{1}{2}$ will shift by the greatest amount during the application of the acceleration correction.

As an example of the application of the acceleration correction to experimental data, a sample of *E. coli* NotI digest was prepared and run on the CS 30 device. The average tag fluorescence traces were plotted for groups of molecules with similar observed length (FIG. 7A, top traces). As a DNA molecule has equal probability of entering the stretching funnel in either orientation, the observed average tag fluorescence traces are expected to appear symmetrical about the center of the average molecule. To exemplify the acceleration induced asymmetry of the raw traces, the fluorescence trace was also inverted and superimposed on the original. This highlights significant asymmetry in each of the selected examples. The amplitude of that asymmetry increases with the length of the selected fragment. For each average trace, acceleration correction was applied using Equation 10. The resulting corrected forward and reverse oriented traces are plotted in FIG. 7A (bottom traces). This demonstrates that the matched traces are superimposable.

Figure 7B:
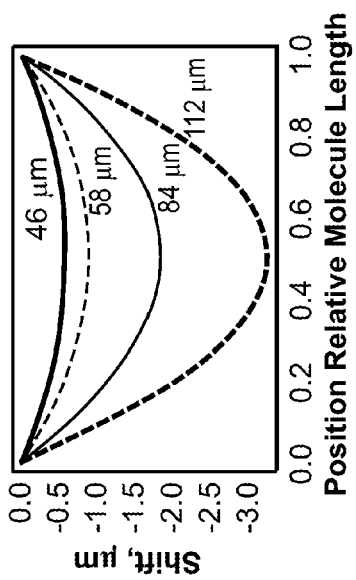
FIG. 7A-7C illustrate the accelerated corrected site specific fluorescence traces.
Figure 7C:
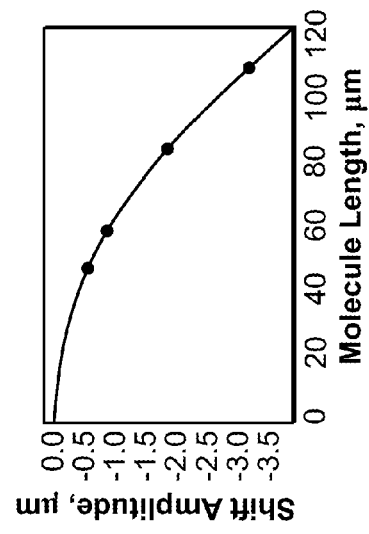
Figure 7A:
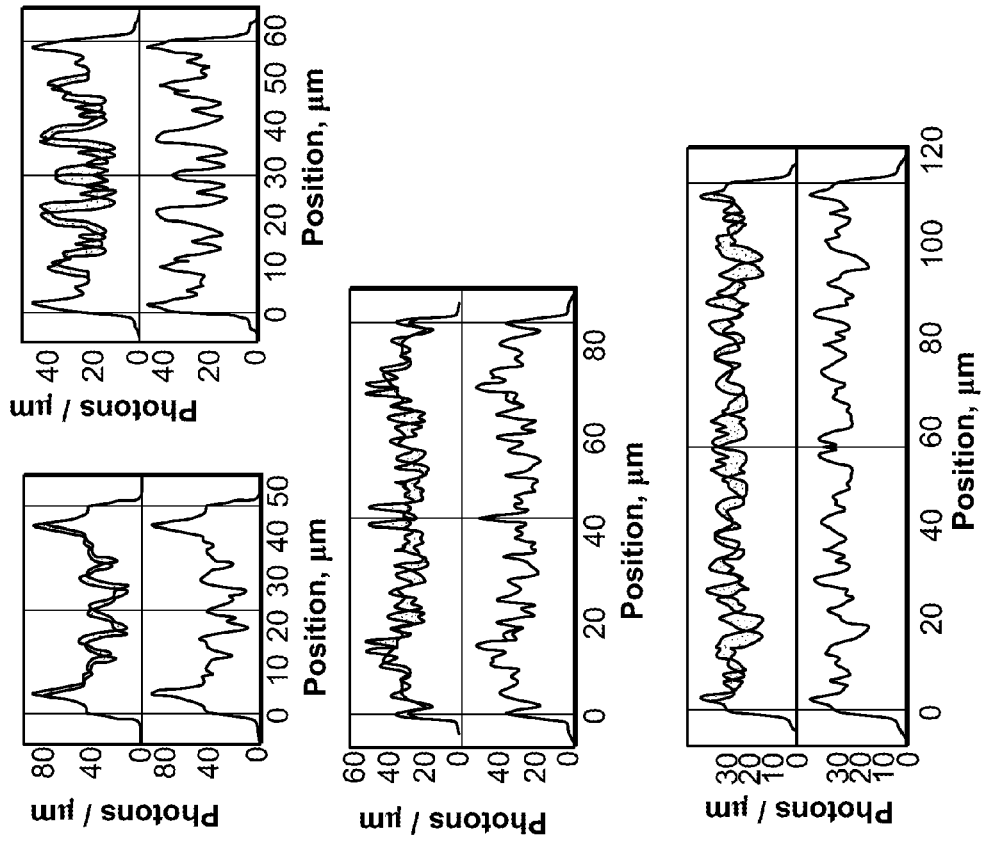

FIG. 7B shows the acceleration correction amplitude along the length of each molecule. Acceleration correction depends only on the tag spot position $x_{tag}$, and the length of the molecule, L. The amplitude of the acceleration correction is, to a good approximation, proportional to the squared fragment length. This dependency is shown in FIG. 7C. The maximum error to this approximation in the tag spot positions with 120 µm molecules is less than 0.05 µm.

Figure 8A:
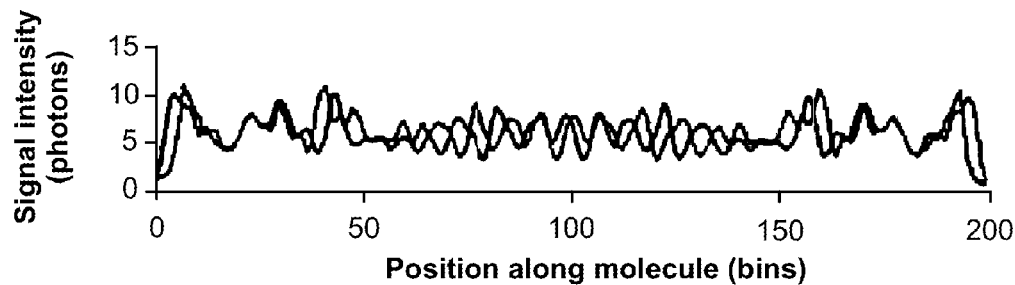
FIGS. 8A-8D illustrates the acceleration correction in constant tension fluidics.
Figure 8B:
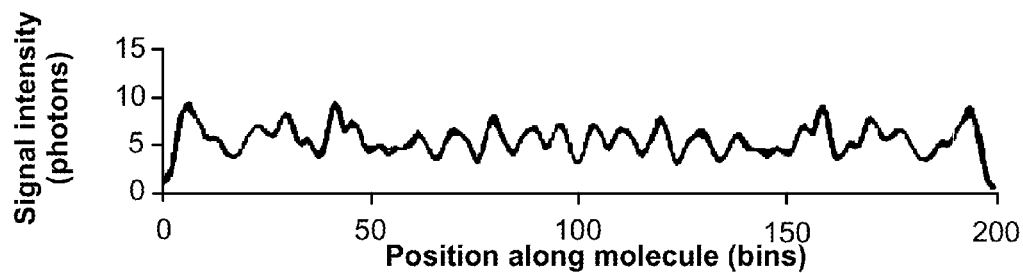

The effect of acceleration dependent signal bias can be readily observed in the average fluorescent signal generated from a cluster of similarly sized molecules. FIG. 8A shows the average tag signal observed in an 85 µm cluster of molecules. Individual molecules generated from a single restriction digest fragment can enter the detection funnel in either a "head first" or "tail first" orientation, with equal probability. Any average trace signal is therefore expected to be symmetrical assuming sufficient detected molecules. When the average signal trace, however, is superimposed on its reverse, the inventors observe that discrete peaks are not directly matched, but appear to be somewhat phase shifted. The amount of this phase shift correction can be computed directly from observed data on a fragment by fragment basis in automated software. Once molecules are corrected for acceleration, the average traces become directly superimposable with its reverse (FIG. 8B).

Figure 8C:
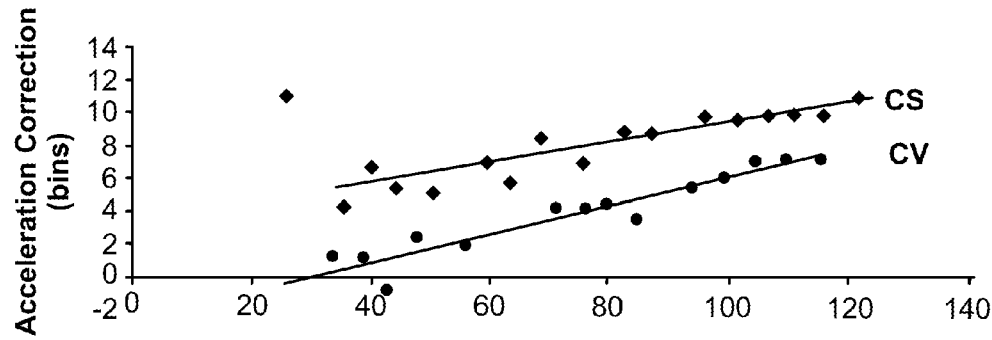
Figure 8D:
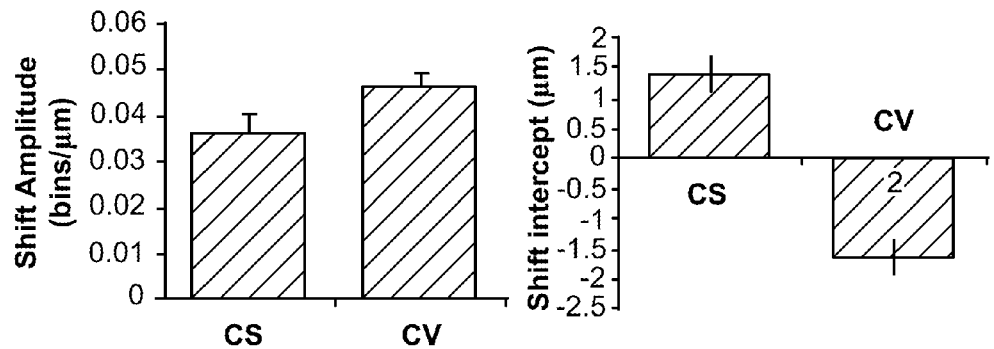

The acceleration correction can be calculated for all molecules within the working fragment range for samples processed on either the CS30 (closed circles) or CV30 devices (open circles, FIG. 8C). The detection spot position was set at the 150 µm position in the CS chip and 50 µm in the CV chip, as described previously. All molecules in the CS device required correction for acceleration, but that correction scaled predictably with fragment length. More strikingly, all analyzed molecules also required acceleration correction in the CV30 device. The slope of the required acceleration correction was comparable to what was required in the CS funnel, but the onset of acceleration correction was shifted towards longer molecules. In the CV funnels, molecules longer than the distance from the onset of the parallel walled channel to the detection point will project into the accelerating strain portion of the funnel. Therefore shorter molecules would be expected to travel at constant velocity but longer molecules would still experience acceleration, thus requiring correction. These observations were repeated using three paired comparisons of CS and CV funnels, and yielded reproducible fits for the acceleration correction in the slope (FIG. 8D) and intercept (FIG. 8E).

Assuming that acceleration correction is required regardless of funnel type, there are significant advantages to applying such corrections in the constant strain rate geometry over the constant velocity geometry. First, the requirement of acceleration correction is uniform for all analyzable molecule lengths. In the constant velocity funnel, the need for acceleration correction is dependent on the precise location of the detection spot in the detection channel. This causes different acceleration correction regimes depending on individual molecule length. Second, because molecules in constant velocity channels experience relaxation of the trailing end, the acceleration correction must accommodate for this distortion as the tail accelerates towards the head of the molecule. Finally, because molecules are observed under constant tension conditions and competing effects of shear-induced tumbling and relaxation are minimized in the CS funnels, the required acceleration correction can be predicted directly for all lengths of DNA from the funnel taper profile.

The inventors have uncovered several developments in the understanding of the behavior of DNA extension in mixed flow microfluidic funnels. There are several key observations. First, DNA extension is dictated by the tension applied to each molecule. This allows for the taper of a stretching funnel to be tailored to any desired fluid velocity and range of molecule lengths. Second, the etched depth of the funnel has competing effects on the efficiency of DNA stretching. The benefits of pre-extension of DNA and reduced rate of molecular relaxation in shallow channels, however may be outweighed by the benefits of reduced fluidic resistance and shear-induced molecular tumbling experienced in deeper channels. Furthermore, application of constant tension detection channels, as the third significant improvement, eliminates any disadvantage incurred by complex shear flow and permits observation of single molecules under constant tension conditions.

Detection under constant tension conditions clearly provides a better physical basis for understanding the mechanics of DNA stretching in extensional flow. Similarly, stretching DNA in constant tension provides a uniform, geometry based framework for the prediction of molecular acceleration. Acceleration correction in constant velocity funnels is much more complicated, as it depends on the length of a DNA molecule, the distance of the detection point from the onset of the constant velocity channel, and also must accommodate any acceleration of the trailing end of the molecule towards the leading end and the molecule begins to relax.

All of the modifications to funnel design serve to significantly improve the throughput of analyzable, well-stretched molecules. According to one embodiment, the ultimate evolution of the funnel design in 2 μm etch depth is the CS50 device. This permits uniform DNA stretching at 50 μm/ms at ~10 psi vacuum. The length range of this device at 50 μm/ms is comparable to that of the CV7.5 at 7.5 μm/ms, representing a 6.66 fold improvement in throughput due to velocity. Changing from a 1 μm to 2 μM etch depth served to double the bulk flow through the DNA injector onto the device, contributing an additional 2 fold improvement. Transitioning from the constant velocity detection channel to the constant strain rate channel also contributes about 2 fold improvement in retention of stretched molecules due to reduced relaxation and hairpinning. In all, through better understanding of DNA stretching in fluidic two-dimensional funnels, the work presented here demonstrates nearly 25 fold improvement in molecule throughput in a simple fluidic device. The throughput improvements demonstrated here are also compatible with microfluidic devices designed to improve molecule throughput by electrokinetic stacking of DNA onto semi-permeable polymer gels and elimination of molecule overlap by fractionation of short, information poor molecules. Improvements in throughput in genomic technology enhances its applicability of detection of rare pathogens in complex bacterial mixtures and in detection from low starting masses of bacterial isolates.

It should be appreciated that various embodiments of the present invention may be formed with one or more of the above-described features. The above aspects and features of the invention may be employed in any suitable combination as the present invention is not limited in this respect. It should also be appreciated that the drawings illustrate various components and features which may be incorporated into various embodiments of the present invention. For simplification, some of the drawings may illustrate more than one optional feature or component. However, the present invention is not limited to the specific embodiments disclosed in the drawings. It should be recognized that the present invention encompasses embodiments which may include only a portion of the components illustrated in any one drawing figure, and/or may also encompass embodiments combining components illustrated in multiple different drawing figures.

It should be understood that the foregoing description of various embodiments of the invention are intended merely to be illustrative thereof and that other embodiments, modifications, and equivalents of the invention are within the scope of the invention recited in the claims appended hereto.

The invention claimed is:

1. A device for stretching at least one polymer in a fluid sample, said device comprising:
    an elongation structure, wherein said elongation structure comprises a tapered channel, said tapered channel decreasing in width from a first end to a second end, said tapered channel comprising:
    a first zone having a first tapered shape;
    a second zone having a second tapered shape, wherein the second tapered shape is different than the first tapered shape; and
    wherein said at least one polymer, when present, moves along said tapered channel from said first end to said second end and is stretched,
    the first tapered shape includes an increasing strain rate taper, and
    the second tapered shape includes a constant strain rate taper.

2. The device of claim 1, wherein the width w(x) of the tapered channel in the second zone is defined by the following equations:

$$w(x) = \frac{w_2}{1 + \frac{x}{a}}$$

$$a = \frac{l_2}{\frac{w_2}{w_3} - 1}$$

wherein $l_2$ is the length of the second zone, $w_2$ is the width of the tapered channel at a transition which separates the first zone from the second zone, and $w_3$ is the width of the tapered channel at the second end of the tapered channel.

3. The device of claim 1, wherein the width w(x) of the tapered channel in the second zone is defined by the following equations:

$$w(x) = \frac{F_2}{x}$$

$$F_2 = \frac{v_x w_x}{\varepsilon}$$

wherein x is distance along the tapered channel, F2 is a constant strain rate taper coefficient, $v_x$ is fluid velocity at distance x, $w_x$ is channel width at distance x, and $\epsilon_x$ is strain rate at distance x.

4. The device of claim 1, wherein the elongation structure is formed on a chip.

5. The device of claim 1, further comprising a delivery region for delivering said at least one polymer in said fluid sample to said elongation structure.

6. The device of claim 5, wherein said delivery region comprises a sample loading port and a delivery channel, said delivery channel leading into the elongation structure.

7. The device of claim 6, further comprising at least one buffer channel leading into the elongation structure.

8. The device of claim 7, wherein the at least one buffer channel comprises at least two opposing buffer channels leading into the elongation structure.

9. A method of stretching at least one polymer in a fluid sample, the method comprising:
delivering a fluid sample into the device recited in claim 1;
stretching the at least one polymer in the first zone of the tapered channel; and
maintaining the tension on the at least one polymer in the second zone of the tapered channel.

10. A method comprising:
moving a polymer through the device recited in claim 1;
detecting an object-dependent impulse that conveys information about structural characteristics of the polymer;
obtaining an observed trace based on the detected impulse, wherein the observed trace is an intensity versus time trace;
applying an acceleration correction to the observed trace; and
obtaining a corrected intensity versus distance trace from the application of the acceleration correction to the observed trace.

11. The method of claim 10, wherein the acceleration correction is defined by:

$$\Delta x_c \cong -\frac{L^2}{2x_{tag}}\tau(1-\tau)$$

wherein:
$\Delta x_c$ is a difference in a distance a molecule would travel assuming a constant velocity compared to a distance traveled in an accelerating flow experienced by the polymer;
L is a length of the molecule;
$x_{tag}$ is a distance of a point of detection from a theoretical asymptotic origin of the constant strain portion of the channel; and τ is a relative time for the molecule to transit a point of detection.

12. A device for stretching at least one polymer in a fluid sample, said device comprising:
an elongation structure, wherein said elongation structure comprises a tapered channel, said tapered channel decreasing in width from a first end to a second end, said tapered channel comprising:
a first zone having a first tapered shape;
a second zone having a second tapered shape, wherein the second tapered shape is different than the first tapered shape; and
wherein said at least one polymer, when present, moves along said tapered channel from said first end to said second end and is stretched,
wherein the first tapered shape includes an increasing strain rate taper, and
wherein a width w(x) of the tapered channel in the first zone is defined by the following equations:

$$w(x) = \frac{1}{(bx+c)^2}$$

$$b = \frac{1}{l_1}\left(\sqrt{\frac{1}{w_2}} - \sqrt{\frac{1}{w_1}}\right)$$

$$c = \sqrt{\frac{1}{w_1}}$$

wherein $l_1$ is the length of the first zone, $w_1$ is the width of the tapered channel at the first end of the tapered channel, and $w_2$ is the width of the tapered channel at a transition which separates the first zone from the second zone.

13. The device of claim 12, wherein the width w(x) of the tapered channel in the second zone is defined by the following equations:

$$w(x) = \frac{w_2}{1 + \frac{x}{a}}$$

$$a = \frac{l_2}{\frac{w_2}{w_3} - 1}$$

wherein $l_2$ is the length of the second zone, $w_2$ is the width of the tapered channel at a transition which separates the first zone from the second zone, and $w_3$ is the width of the tapered channel at the second end of the tapered channel.

14. The device of claim 12, wherein the width w(x) of the tapered channel in the second zone is defined by the following equations:

$$w(x) = \frac{F_2}{x}$$

$$F_2 = \frac{v_x w_x}{\varepsilon}$$

wherein x is distance along the tapered channel, $F_2$ is a constant strain rate taper coefficient, $v_x$ is fluid velocity at distance x, $w_x$ is channel width at distance x, and $\epsilon_x$ is strain rate at distance x.

15. A device for stretching at least one polymer in a fluid sample, said device comprising:
an elongation structure, wherein said elongation structure comprises a tapered channel, said tapered channel decreasing in width from a first end to a second end, said tapered channel comprising:
a first zone having a first tapered shape;
a second zone having a second tapered shape, wherein the second tapered shape is different than the first tapered shape; and
wherein said at least one polymer, when present, moves along said tapered channel from said first end to said second end and is stretched,
wherein the first tapered shape includes an increasing strain rate taper, and
wherein a width w(x) of the tapered channel in the first zone is defined by the following equations:

$$w(x) = \frac{2w_i v_i}{ax^2} = \frac{F_1}{x^2}$$

$$F_1 = \frac{2v_x w_x x}{\dot{\epsilon}_x}$$

wherein x is distance along the channel, $w_i$ is channel width at arbitrary position i, $v_i$ is fluid velocity at arbitrary position i, F1 is a geometrical taper coefficient for an increasing strain rate funnel, $v_x$ is fluid velocity at distance x, $w_x$ is channel width at distance x, and $\epsilon_x$ is strain rate at distance x.

16. The device of claim 15, wherein the width w(x) of the tapered channel in the second zone is defined by the following equations:

$$w(x) = \frac{w_2}{1 + \frac{x}{a}}$$

$$a = \frac{l_2}{\frac{w_2}{w_3} - 1}$$

wherein $l_2$ is the length of the second zone, $w_2$ is the width of the tapered channel at a transition which separates the first zone from the second zone, and $w_3$ is the width of the tapered channel at the second end of the tapered channel.

17. The device of claim 15, wherein the width w(x) of the tapered channel in the second zone is defined by the following equations:

$$w(x) = F_2/x$$

$$F_2 = v_x w_x / \dot{\epsilon}$$

wherein x is distance along the tapered channel, $F_2$ is a constant strain rate taper coefficient, $v_x$ is fluid velocity at distance x, $w_x$ is channel width at distance x, and $\epsilon_x$ is strain rate at distance x.

18. A device for stretching at least one polymer in a fluid sample, said device comprising:
an elongation structure, wherein said elongation structure comprises a tapered channel, said tapered channel having a width w(x) which decreases from a first end to a second end, the tapered channel comprising:
a first zone having a first shape;
a second zone having a second shape, wherein the second shape is different than the first shape; and
a transition which separates the first zone from the second zone;
wherein the width w(x) of the tapered channel in the first zone is defined by the following equations:

$$w(x) = \frac{1}{(bx+c)^2}$$

$$b = \frac{1}{l_1}\left(\sqrt{\frac{1}{w_2}} - \sqrt{\frac{1}{w_1}}\right)$$

$$c = \sqrt{\frac{1}{w_1}}$$

wherein $l_1$ is the length of the first zone, $w_1$ is the width of the tapered channel at the first end of the tapered channel, and $w_2$ is the width of the tapered channel at the transition;
wherein the width w(x) of the tapered channel in the second zone is defined by the following equations:

$$w(x) = \frac{w_2}{1 + \frac{x}{a}}$$

$$a = \frac{l_2}{\frac{w_2}{w_3} - 1}$$

and wherein $l_2$ is the length of the second zone, $w_2$ is the width of the tapered channel at the transition, and $w_3$ is the width of the tapered channel at the second end of the tapered channel.

19. The device of claim 18, wherein the elongation structure is formed on a chip.

20. The device of claim 18, further comprising a delivery region for delivering said at least one polymer in said fluid sample to said elongation structure.

21. The device of claim 20, wherein said delivery region comprises a sample loading port and a delivery channel, said delivery channel leading into the elongation structure.

22. The device of claim 21, further comprising at least one buffer channel leading into the elongation structure.

23. The device of claim 22, wherein the at least one buffer channel includes two opposing buffer channels leading into the elongation structure.

* * * * *